United States Patent

Kordis et al.

[11] Patent Number: 5,904,680
[45] Date of Patent: *May 18, 1999

[54] MULTIPLE ELECTRODE SUPPORT STRUCTURES HAVING OPTIMAL BIO-MECHANICAL CHARACTERISTICS

[75] Inventors: Thomas F. Kordis, San Jose; Dorin Panescu, Sunnyvale; James G. Whayne, Saratoga, all of Calif.

[73] Assignee: EP Technologies, Inc., Sunnyvale, Calif.

[*] Notice: This patent is subject to a terminal disclaimer.

[21] Appl. No.: 08/557,790

[22] Filed: Nov. 13, 1995

Related U.S. Application Data

[63] Continuation-in-part of application No. 08/206,414, Mar. 4, 1994, abandoned, which is a continuation-in-part of application No. 08/033,640, Mar. 16, 1993, abandoned, and a continuation-in-part of application No. 08/168,476, Dec. 16, 1993, Pat. No. 5,509,419, which is a division of application No. 07/951,157, Sep. 25, 1992, Pat. No. 5,309,910.

[51] Int. Cl.⁶ .................................................. A61B 17/36
[52] U.S. Cl. ........................... 606/41; 607/122; 600/374
[58] Field of Search ................................ 606/41, 42, 45, 606/1, 50; 607/115, 116, 122; 128/642; 600/374

[56] References Cited

U.S. PATENT DOCUMENTS

| | | |
|---|---|---|
| 3,326,207 | 6/1967 | Egan . |
| 3,517,128 | 6/1970 | Hines . |
| 3,557,794 | 1/1971 | Van Patten . |
| 4,360,031 | 11/1982 | White . |
| 4,522,212 | 6/1985 | Gelinas et al. . |
| 4,628,937 | 12/1986 | Hess et al. . |
| 4,649,924 | 3/1987 | Taccardi . |
| 4,660,571 | 4/1987 | Hess et al. . |
| 4,664,120 | 5/1987 | Hess . |
| 4,690,148 | 9/1987 | Hess . |
| 4,699,147 | 10/1987 | Chilson et al. ........................ 607/122 |
| 4,940,064 | 7/1990 | Desai . |
| 4,976,710 | 12/1990 | Mackin . |
| 5,010,894 | 4/1991 | Edhag . |
| 5,156,151 | 10/1992 | Imran . |
| 5,228,442 | 7/1993 | Imran . |
| 5,263,493 | 11/1993 | Avitall . |
| 5,309,910 | 5/1994 | Edwards et al. . |
| 5,313,943 | 5/1994 | Houser et al. . |
| 5,324,284 | 6/1994 | Imran . |
| 5,327,889 | 7/1994 | Imran . |
| 5,345,936 | 9/1994 | Pomeranz et al. . |
| 5,365,926 | 11/1994 | Desai . |
| 5,383,917 | 1/1995 | Desai et al. . |
| 5,411,025 | 5/1995 | Webster, Jr. . |
| 5,433,198 | 7/1995 | Desai . |
| 5,454,370 | 10/1995 | Avitall . |
| 5,465,717 | 11/1995 | Imran et al. . |
| 5,549,108 | 8/1996 | Edwards et al. . |
| 5,647,870 | 7/1997 | Kordis et al. .............................. 606/41 |

FOREIGN PATENT DOCUMENTS

| | | |
|---|---|---|
| 4025-369 | 9/1990 | Germany . |
| WO94/12098 | 6/1994 | WIPO . |
| WO94/21168 | 9/1994 | WIPO . |
| WO96/25094 | 8/1996 | WIPO . |

*Primary Examiner*—Michael Peffley
*Attorney, Agent, or Firm*—Lyon & Lyon LLP

[57] ABSTRACT

An electrode support structure comprises a distal hub and a proximal base aligned along a major axis with the distal hub. An array of generally flexible spline elements extend between the hub and the base. The spline elements each have an elongated axis that, at the base, extends generally parallel to the major axis and, at the hub, extends at an angle, measured relative to the major axis, of between 45° and 110°. The spline elements collectively define a distal surface lying within an envelope that approximates the curvature of endocardial tissue and within which envelope the distal hub lies. According to this aspect of the invention, the distal surface, when contacting endocardial tissue, increases in surface area in response to force applied generally along the major axis to mediate tissue pressure.

14 Claims, 23 Drawing Sheets

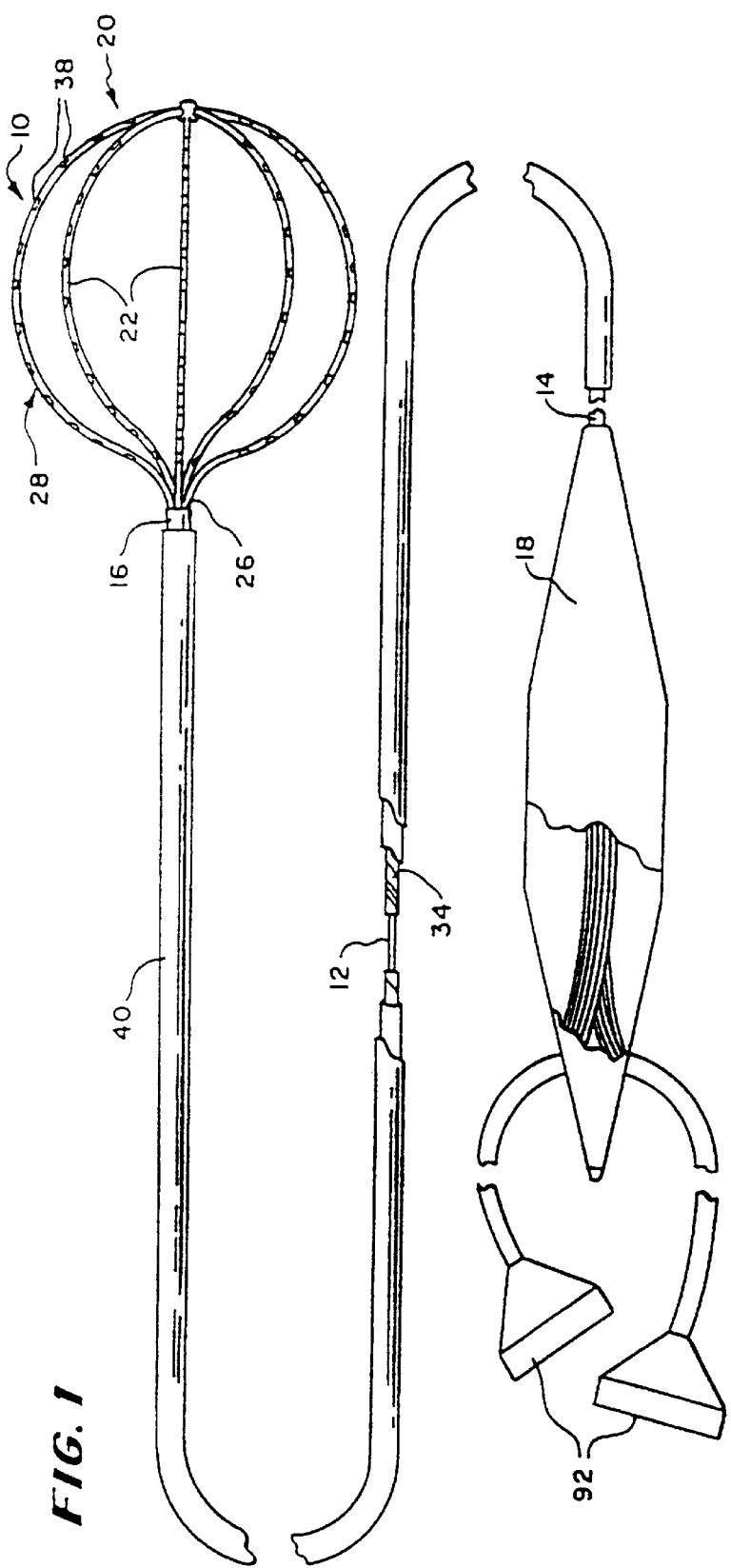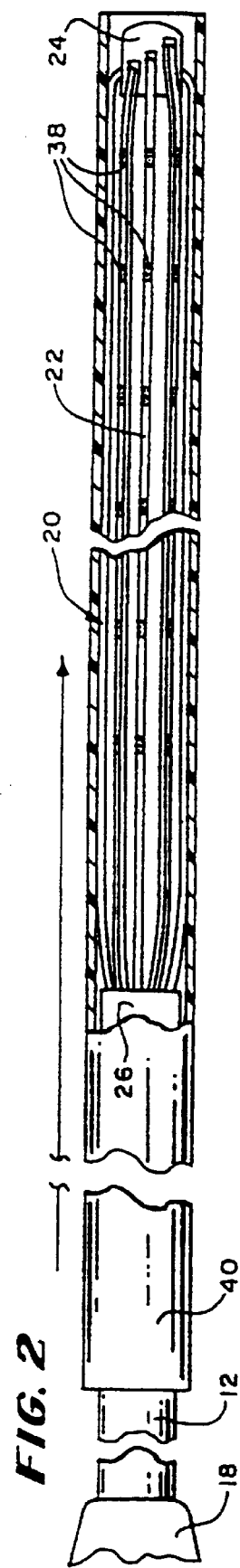

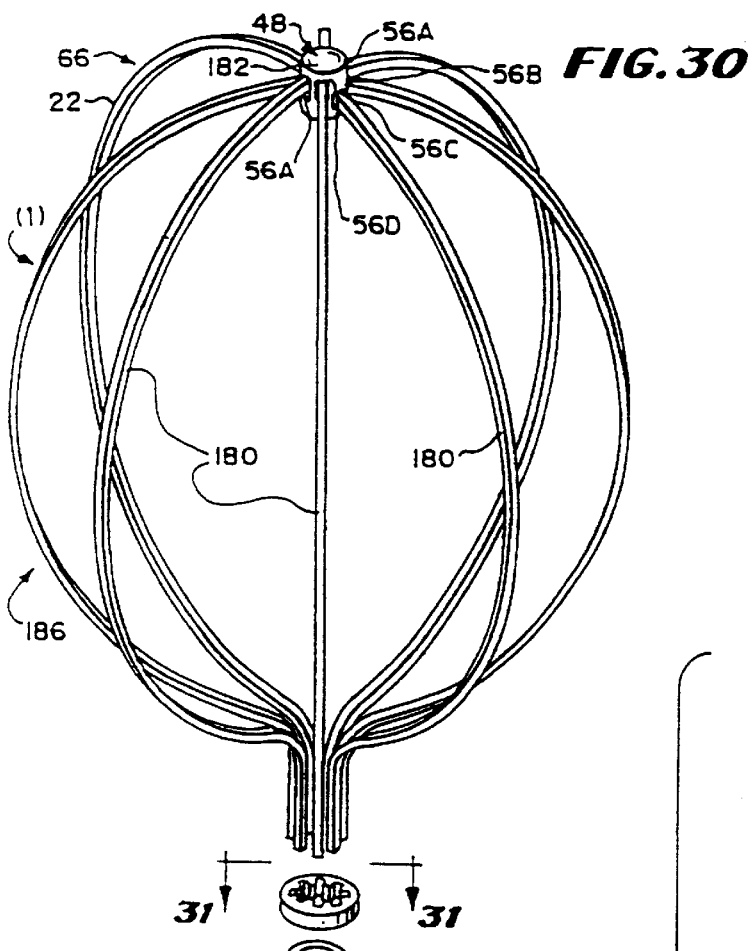
FIG. 30
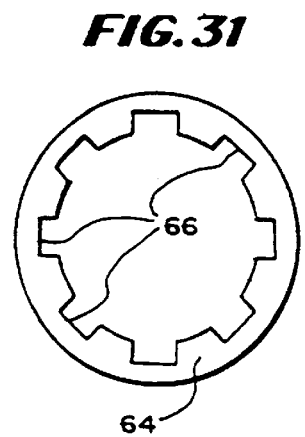
FIG. 31
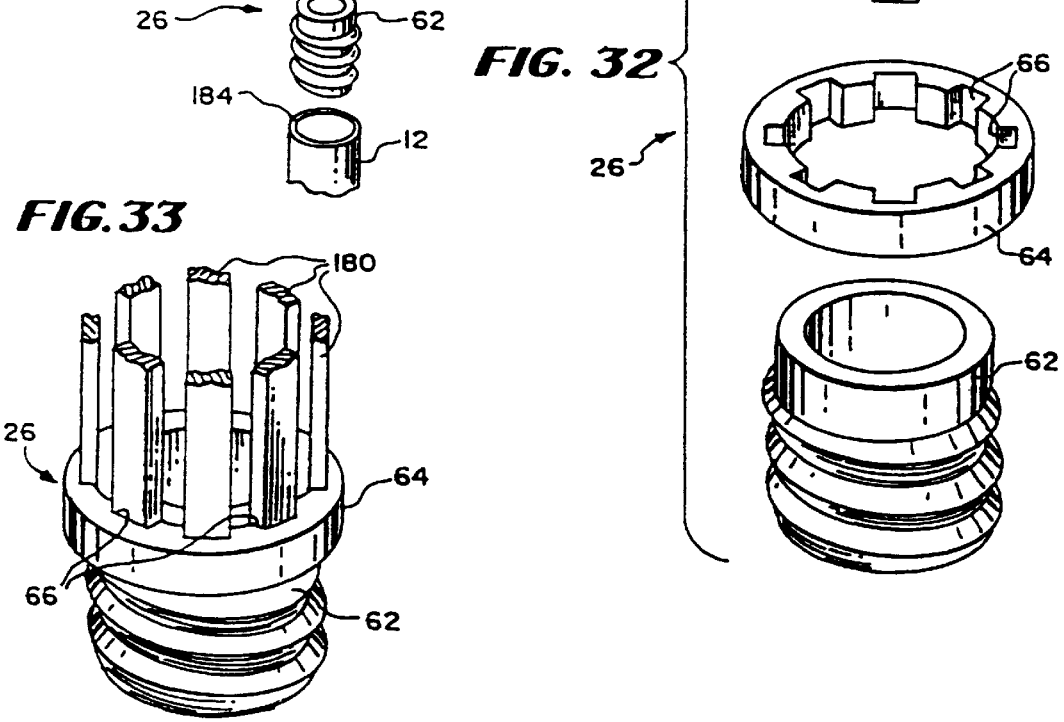
FIG. 32
FIG. 33

FIG. 44.

| | | OVERALL STIFFNESS TABULATION | | | | | | | |
|---|---|---|---|---|---|---|---|---|---|
| | | Structure 190 | | Structure 190 | | Structure 186 | | Structure 186 | |
| Chart | Condition | Slope gm/mil | Intercept grams | Slope gm/mil | Intercept grams | Slope gm/mil | Intercept grams | Slope gm/mil | Intercept grams | Stiffness Ratio |
| | Wire Pulled | | | | | | | | | |
| 1 | Unconstrained | 0.09 | 48.89 | 0.09 | 44.94 | 0.04 | 3.45 | 0.04 | 4.04 | 2.4 |
| 2 | 1.44" ID Tube | 7.97 | 3.58 | - | - | 0.63 | 3.13 | - | - | 12.7 |
| 3 | 1.19" ID Tube | 9.95 | 28.83 | - | - | 0.92 | 7.88 | 0.87 | 1.25 | 10.8 |
| 4 | .94" ID Tube | 9.45 | -3.12 | - | - | 1.12 | 3.83 | 0.77 | 1.68 | 8.4 |
| 5 | .69" ID Tube | 11.87 | -87.13 | - | - | 4.45 | 2.33 | - | - | 2.7 |
| 6 | Single Spline side | 0.42 | 8.79 | 0.42 | 2.57 | 0.05 | 2.08 | 0.07 | 2.21 | 5.7 |
| 7 | Torque | 0.51 | 0.00 | 0.53 | 0.00 | 0.19 | 0.00 | 0.18 | 0.00 | 2.6 |
| | Wire Free | | | | | | | | | |
| 3 | 1.19" ID Tube | 2.71 | 29.45 | | | | | | | |
| 4 | .94" ID Tube | 5.56 | -4.70 | | | | | | | |

MULTIPLE ELECTRODE SUPPORT STRUCTURES HAVING OPTIMAL BIO-MECHANICAL CHARACTERISTICS

RELATED APPLICATION

This application is a continuation-in-part of application Ser. No. 08/206,414, filed Mar. 4, 1994, now abandoned, which is a continuation-in-part of Ser. No. 08/033,640, filed Mar. 16, 1993, now abandoned. This application is also a continuation-in-part of Ser. No. 08/168,476, filed Dec. 16, 1993, now U.S. Pat. No. 5,509,419, issued Apr. 23, 1996, which is a divisional of application Ser. No. 07/951,157, filed Sep. 25, 1992, now U.S. Pat. No. 5,309,910, issued May 10, 1994.

FIELD OF THE INVENTION

The invention relates to multiple electrode structures deployed in interior regions of the heart for diagnosis and treatment of cardiac conditions.

BACKGROUND OF THE INVENTION

Physicians make use of catheters today in medical procedures to gain access into interior regions of the body to ablate targeted tissue areas. It is important for the physician to be able to precisely locate the catheter and control its emission of energy within the body during tissue ablation procedures.

The need for precise control over the catheter is especially critical during procedures that ablate endocardial tissue within the heart. These procedures, called electrophysiological therapy, are use to treat cardiac rhythm disturbances.

During these procedures, a physician steers a catheter through a main vein or artery into the interior region of the heart that is to be treated. The physician then further manipulates a steering mechanism to place the electrode carried on the distal tip of the catheter into direct contact with the endocardial tissue that is to be ablated. The physician directs energy from the electrode through tissue either to an indifferent electrode (in a uni-polar electrode arrangement) or to an adjacent electrode (in a bi-polar electrode arrangement) to ablate the tissue and form a lesion.

Physicians examine the propagation of electrical impulses in heart tissue to locate aberrant conductive pathways and to identify foci, which are ablated. The techniques used to analyze these pathways and locate foci are commonly called "mapping."

Conventional cardiac tissue mapping techniques introduce several linear electrode arrays into the heart through vein or arterial accesses. There remains a need for improved endocardial mapping techniques using three dimensional, multiple electrode structures.

An endocardial multiple electrode mapping structure can potentially remain in place within a heart chamber for ten thousand to twenty thousand heart beats. During this time, the powerful contractions of heart muscle constantly flex and stress the structure. The structure must be strong and flexible enough to survive introduction and fatigue in this dynamic environment. The structure also must be designed to keep the electrodes spaced apart both longitudinally and circumferentially without failure and without shedding parts. Though strong and durable, the structures also must cause no trauma when in contact with tissue.

While prior multiple electrode support structures may attempt to provided the requisite strength and flexibility, they have created envelopes with blunt, non-conforming contours that can poke into tissue and cause trauma during heart contractions.

It can be seen that providing economical, durable, and safe multiple electrodes in a package small enough to be deployed within the heart poses often conflicting challenges.

SUMMARY OF THE INVENTION

This invention has as its principal objective the realization of safe and efficacious endocardial mapping techniques.

The invention provides structures for supporting multiple electrode arrays within the heart that address the conflicting challenges. They optimize mechanical characteristics of the structures to best achieve the intended electrophysiological function, while also avoiding tissue trauma. At the same time, they possess minimal structural parts and complexity, lending themselves to practical, economical fabrication techniques.

One aspect of the invention provides an electrode support structure comprising a distal hub and a proximal base aligned along a major axis with the distal hub. A generally flexible spline element extends between the hub and the base the spline element. The spline has an elongated axis that, at the base, extends generally parallel to the major axis and, at the hub, extends at an angle, measured relative to the major axis, of between 45° and 110°. This geometry lends significant stability to the structure, imparting to the spline element the capability of deforming in response to radial, lateral, and torsional forces without buckling or warping.

Another aspect of the invention provides an electrode support structure comprising a distal hub having an opening and a proximal base. A generally flexible spline element extends between the hub and the base. According to this aspect of the invention, the spline element is flexibly constrained within the opening against movement out of the opening. Nevertheless, the opening has clearance to accommodate twisting of the spline element within the opening in response to external force. This measure of flexible, "soft" constraint at the distal end of the structure lessens the overall stiffness of the structure. It imparts to the structure tha ability to flexibly deform, without buckling or warping, in response to complex radial, lateral, and torsional forces.

Yet another aspect of the invention provides an electrode support structure comprising a distal hub and a proximal base aligned along a major axis with the distal hub. An array of generally flexible spline elements extend between the hub and the base. The spline elements each have an elongated axis that, at the base, extends generally parallel to the major axis and, at the hub, extends at an angle, measured relative to the major axis, of between 45° and 110°. The spline elements collectively define a distal surface lying within an envelope that approximates the curvature of endocardial tissue and within which envelope the distal hub lies. According to this aspect of the invention, the distal surface, when contacting endocardial tissue, increases in surface area in response to force applied generally along the major axis to mediate tissue pressure.

Other features and advantages of the inventions are set forth in the following Description of the Drawings, as well as in the appended claims.

BRIEF DESCRIPTION AND DRAWINGS

FIG. 1 is a plan view of a multiple electrode probe that embodies the features of the invention, showing the associated electrode support assembly in its deployed condition;

FIG. 2 is an enlarged view of the distal end of the probe shown in FIG. 1, showing the associated electrode support assembly in a collapsed condition within a sliding outer sleeve;

FIG. 30 is an exploded perspective view of the electrode support assembly assembled from several hoop-like bodies shown in FIG. 23 using the end cap shown in FIG. 25 and a base;

FIG. 31 is a lock ring associated with the base for the support assembly shown in FIG. 30, taken generally along line 31—31 in FIG. 30;

FIG. 32 is an exploded perspective view of the lock ring and anchor member of the base for the electrode support assembly shown in FIG. 30;

FIG. 33 is an assembled perspective view of the lock ring and anchor member of the base for the electrode support assembly shown in FIG. 30;

FIG. 44 is a table listing the stiffnesses measured for a preferred structure and another structure.

Figure 3:
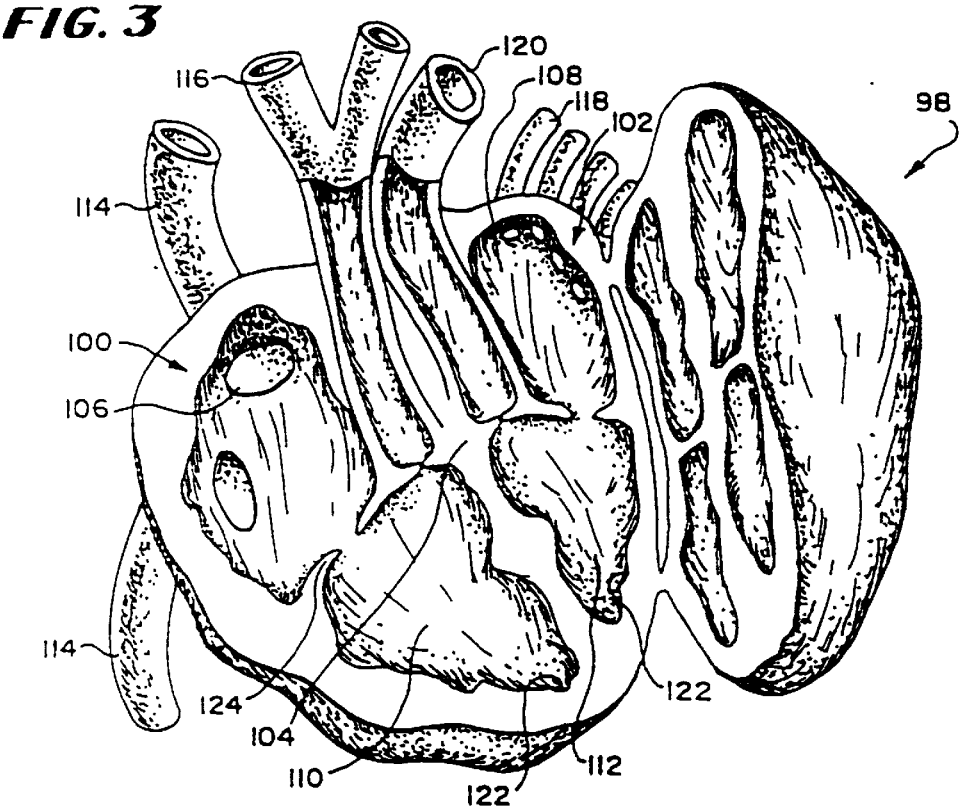
FIG. 3 is a diagrammatic sectional view of the interior of a human heart at diastole.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

I. Overview of the Electrode Support Assembly

FIG. 1 shows a multiple electrode probe 10 that embodies the features of the invention.

The probe 10 includes a flexible catheter tube 12 with a proximal end 14 and a distal end 16. The proximal end 14 carries an attached handle 18. The distal end 16 carries an electrode support assembly 20.

The electrode support assembly 20 comprises an array of flexible spline elements 22 assembled to form a three dimensional structure. The spline elements 22 radiate between a distal tip 24 and a base 26, which the distal end 16 of the catheter tube 12 carries. The support assembly 20 retains the spline elements 22 in a three dimensional basket structure. Of course, the resulting structure can assume other shapes.

The probe 10 also includes an electrode circuit assembly 28, one for each spline 22. Each circuit assembly 28 includes an array of multiple electrodes 38. The electrodes 38 are connected by signal wires 34, which extend through the catheter tube 12, to external connectors 92, which the handle 18 carries. Further details of the construction of the electrode circuit assemblies are shown in pending U.S. application Ser. No. 08/206,414, filed Mar. 4, 1994, which is incorporated herein by reference.

When deployed for use (as FIG. 1 shows) —which, in the preferred embodiment, is inside a heart chamber—the support assembly 20 holds the electrodes 38 in intimate contact against the endocardium.

In the illustrated and preferred embodiment, the probe 10 includes an outer sheath 40 carried about the catheter tube 12. As FIG. 2 best shows, the sheath 40 has an inner diameter that is greater than the outer diameter of the catheter tube 12. As a result, the sheath 40 slides along the catheter tube 12.

As FIG. 2 shows, forward movement advances the slidable sheath 40 over the support assembly 20. In this position, the slidable sheath 40 compresses and collapses the support assembly 20 for introduction through a vein or artery to the intended treatment site within the body.

As FIG. 1 shows, rearward movement retracts the slidable sheath 40 away from the support assembly 20. This removes the compression force. The freed support assembly 20 opens and assumes its three dimensional shape.

II. Desired Bio-Mechanical Characteristics for the Support Assembly

A. The Biological Environment

The heart 98 (see FIGS. 3 and 4) is divided into a right side 100 and a left side 102 by the cardiac septum 104. Each right and left side contains an upper blood collecting chamber, called the atrium, respectively 106 and 108. Each right and left side also contains a lower blood pumping chamber, called the ventricle, respectively 110 and 112. The right atrium 106 receives oxygen-depleted blood from the body through the vena cava 114. The right ventricle 110 pumps the oxygen-depleted blood to the lungs through the pulmonary artery 116, where the blood is oxygenated. The left atrium 108 receives oxygenated blood from the lungs from the pulmonary veins 118. The left ventricle 112 pumps the oxygenated blood to the body through the aorta 120.

The heart muscle pumps the blood by means of rhythmical dilations, called diastole, and contractions, called systole.

Figure 4:
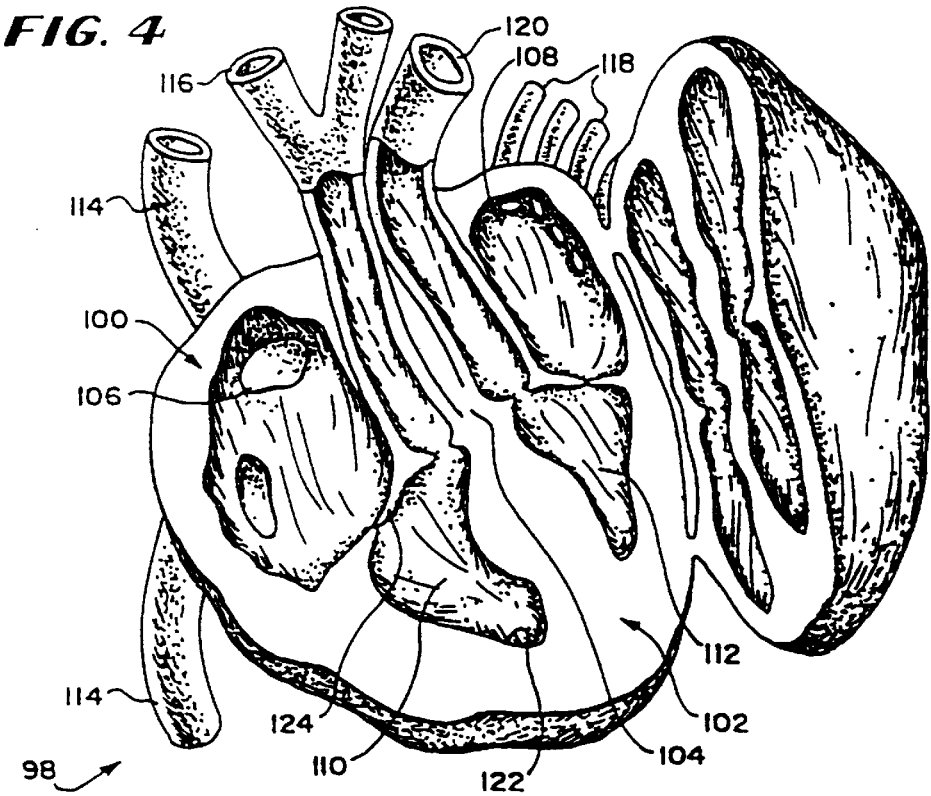
FIG. 4 is a diagrammatic sectional view of the interior of a human heart at ventricular systole.

During ventricular diastole (as FIG. 3 shows), the ventricles 110 and 112 are flaccid, and blood enters both the atria 106 and 108 and the ventricles 110 and 112. At the end of ventricular diastole, the atria 106 and 108 contract and thus help to fill the ventricles 110 and 112. This is followed by ventricular systole (as FIG. 4 shows). During ventricular systole, the ventricles 110 and 112 contract, and blood is pumped from the right ventricle 110 to the lungs and from the left ventricle 112 to the body.

In a healthy heart, the entire cardiac cycle takes about 0.9 second. In adults at rest, there are between 60 and 74 beats a minute. In infants and young children it may be between 100 and 120 beats a minute.

During contraction, the interior walls of the heart chambers deform, as FIG. 4 shows. The chambers contract along the vertical axis while contracting even more about the axis. The degree to which a given chamber deforms depends upon the size and morphology of the heart and whether the chamber is an atrium or ventricle. Deformation is most pronounced in the ventricles, where the major pump action occurs. Typically, during systole, a ventricle contracts as much as 10% along its vertical axis, while reducing its interior diameter by as much as 50%.

Furthermore, during systole, the heart muscle in the chamber contracts in a progressive, peristaltic fashion. The contraction begins near the chamber inlet valve and progresses toward the chamber outlet valve. In the ventricle, the apex 122 (shown in FIGS. 3 and 4) also twists approximately 15° with respect to the base 124 in a "wringing" motion during systole.

Figure 5:
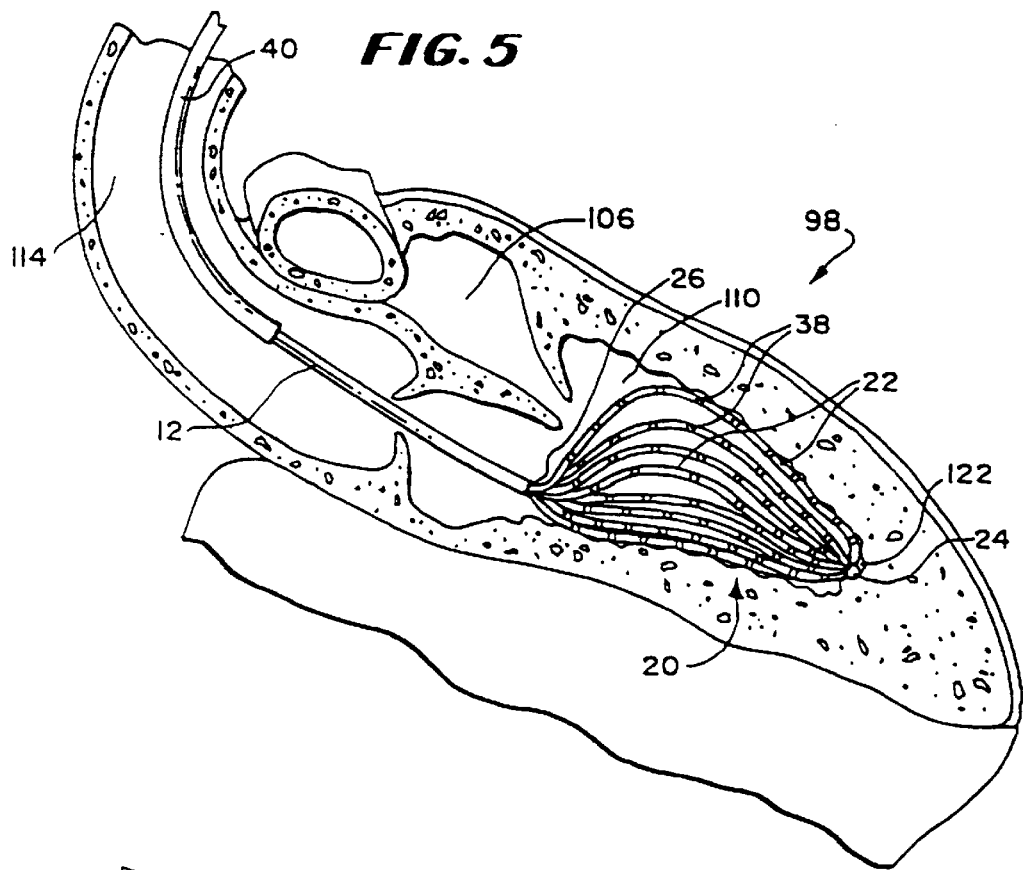
FIG. 5 is a diagrammatic section of the interior of the right side of the human heart in diastole with a preferred multiple electrode structure deployed.
Figure 6:
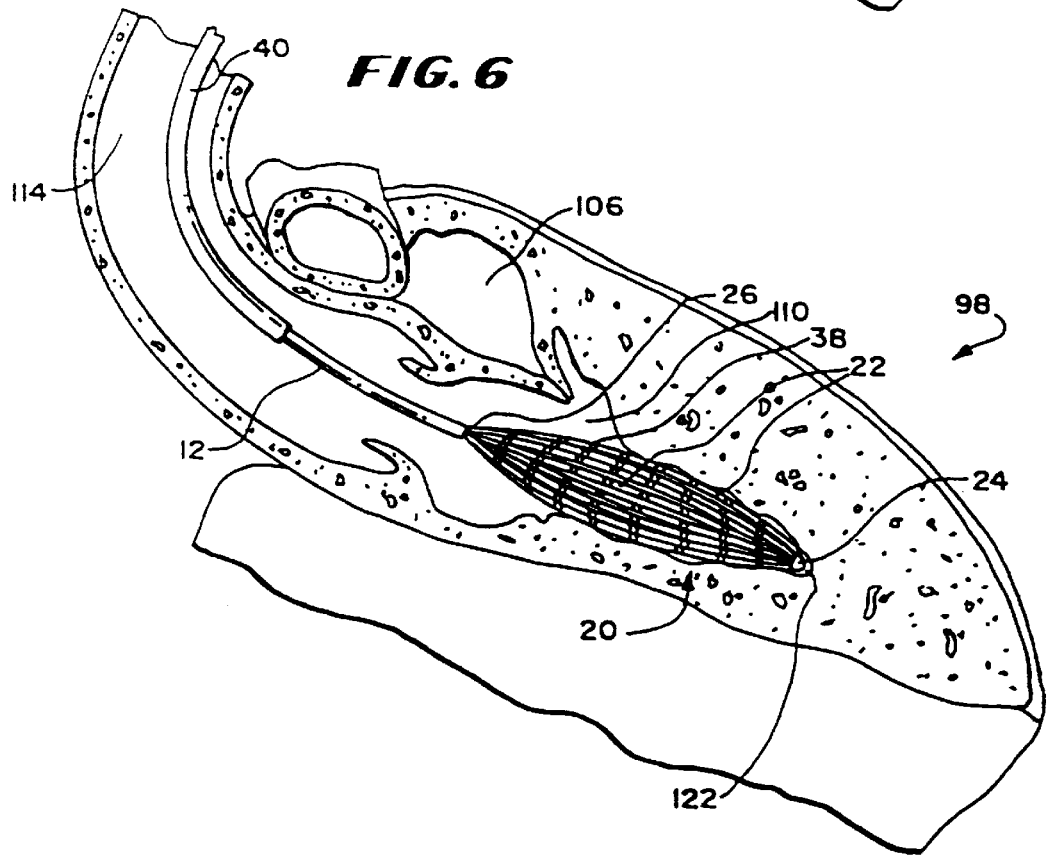
FIG. 6 is a diagrammatic section of the interior of the right side of the human heart in systole with the preferred multiple electrode structure, also shown in FIG. 5, deployed.

As FIGS. 5 and 6 demonstrate, the biological forces within the heart 98 create a dynamic environment in which the structure 20 shown in FIG. 1 must function. Exposed to these constant, complex radial and axial forces within the heart 98 (which FIGS. 5 and 6 depict, respectively, during diastole and systole in the right ventricle 110), the structure 20 must possess the mechanical properties to maintain the electrodes 38 in intimate contact against the endocardium in a stable, fixed location. Loss of contact can produce motion artifacts and a breakdown of intended function.

Nonstationary contact also introduces uncertainty about the position of the electrodes 38. The physician cannot be certain that information obtained from one location during a beat comes from the same location in the next beat. Again, a breakdown of intended function occurs.

The failure to maintain intimate contact also enhances the risk of trauma. Repeated movement and sliding of the structure 20 across and against the endocardium and interior trabecula and teandonae can lead to perforation or tamponade if the trauma is severe enough. Less severe trauma can still locally injure tissue, increasing the likelihood of clot formation and potential emboli.

To uniformly conform to the endocardium during systole (as FIG. 6 shows), the structure 20 should have the mechanical characteristics to tolerate significant deformation. The structure 20 should be free to move radially inwards while shortening axially. During diastole (as FIG. 5 shows), the structure 20 should possess the mechanical characteristic to spring back, as the endocardium returns outwards into its original shape. The structure 20 must also have the capability to resist sliding or "walking" toward the apex 122 during the progressive, peristaltic forces of systole, which push and pull and twist the structure 20. Overriding this complex set of mechanical characteristics is the requirement to minimize the incidence of trauma.

B. Desired Bio-Mechanical Characteristics

The invention has characterized important mechanical properties for a multiple electrode structure 20 like that shown in FIG. 1 to perform its intended biological function without trauma in the human heart. The invention expresses these properties in terms of a set of bio-mechanical functions.

The invention also quantifies some of the bio-mechanical functions. The quantified bio-mechanical function values determine the capability of a given structure 20 to perform its intended function in the dynamic environment of an in vivo heart.

The invention divides the bio-mechanical functions into three main categories. The first category pertains to bio-mechanical functions of the individual splines 22 themselves. The second category of bio-mechanical functions pertains to the mechanical characteristics the integrated structure 20 the assembled splines 22 create. The third category of bio-mechanical functions pertains to the geometry of the splines 22 when constrained between the distal tip 24 and the base 26 of the structure 20.

The first category of bio-mechanical functions includes:

(i) the spline radial stiffness function $S_r$. From a mechanical standpoint, the value of $S_r$ expresses the ability of an individual spline 22 to deform radially of its axis. From a bio-mechanical standpoint, the value of $S_r$ determines the ability of an individual spline 22 to follow the contour of the endocardium independent of other splines 22 during systole and diastole while causing no trauma.

(ii) the spline lateral stiffness function $S_l$ From a mechanical standpoint, the value of $S_l$ expresses the ability of an individual spline 22 to twist-deform about its axis. From a bio-mechanical standpoint, the value of $S_l$ determines the ability of an individual spline 22 to deform around surface structures on the endocardium, like trabeculae, cardae tendineae, and papillary muscles. From a bio-mechanical standpoint, the value of $S_l$ also determines the ability of an individual spline 22 to present and maintain electrodes in intimate contact with the endocardium while avoiding trauma.

The second category of bio-mechanical functions includes:

(i) the torsional stiffness function $T_t$. From a mechanical standpoint, the value of $T_t$ expresses the ratio between torque and angular deflection of the distal tip 24 with respect to the base of the structure 20. From a bio-mechanical standpoint, the value of $T_t$ determines the ability of the structure 20 to follow the "wringing" motion of a ventricle during systole.

(ii) the tissue force function $T_f$. From a mechanical standpoint, the value of $T_f$ expresses the force exerted on tissue contacting the distal tip 24 of the structure 20 as a function of the structure diameter and forced deflection of the distal tip 24. From a bio-mechanical standpoint, the value of $T_f$ determines the ability of the distal tip 24 of the structure 20 to conform to both the diastolic and systolic shape of a heart chamber without becoming a rigid stent structure.

(iii) the tissue pressure function $T_p$. From a mechanical standpoint, the value of $T_p$ expresses the pressure exerted on tissue contacting the distal tip 24 of the structure 20 as a function of the structure diameter and forced deflection of the distal tip 24. From a bio-mechanical standpoint, the value of $T_p$ determines the ability of the distal tip 24 of the structure 20 to contact tissue during deployment and the cardiac cycle without perforation or tamponade.

The third category of bio-mechanical functions includes:

(i) the components of the spline 22. From a mechanical standpoint, the components of the spline 22 typically include a core body made from resilient, inert wire or plastic, a surrounding sleeve of plastic tubing, and associated electrodes and signal wires. Each individual component contributes in some degree to the overall ability of the spline 22 to react to radial and torsional forces. From a bio-mechanical standpoint, the bio-mechanical properties of each individual component should be understood to ascertain the degree to which these individual bio-mechanical properties affect the overall bio-mechanical properties of the spline 22.

(ii) the cross section geometry of the splines 22. From a mechanical standpoint, the spline's cross section geometry affects the ability of the spline 22 to react to radial and torsional forces without irregular physical deformation, warping, or buckling. From a bio-mechanical standpoint, the cross section geometry is one factor that helps to determine the ability of the spline 22 to deform without loss of desired mechanical characteristics in a heart chamber.

(iii) the axial geometry of the spline 22 when constrained between the distal tip and base of the structure 20. From a mechanical standpoint, the axial geometry of the spline 22, like its cross section geometry, is another factor that determines the ability of the spline 22 to withstand radial and torsional forces without irregular physical deformation, warping, or buckling. From a bio-mechanical standpoint, the axial geometry of the constrained spline structure 20, like the cross section geometry, determines the overall stability of the structure 20 during exposure to diastolic and systolic forces in a heart chamber.

1. Bio-Mechanical Functions for Individual Splines a. Spline Radial Force Function $S_r$ The spline radial stiffness function $S_r$ (see FIGS. 7 and 8) expresses the ratio between radial force ($F_r$) applied to the spline 22 perpendicular to the axis of the structure 20 and the radial distance ($D_r$) the spline 22 deflects toward the axis of the spline 22 in response to the radial force. That is:

$$S_r = \frac{F_r}{D_r}$$

Figure 7:
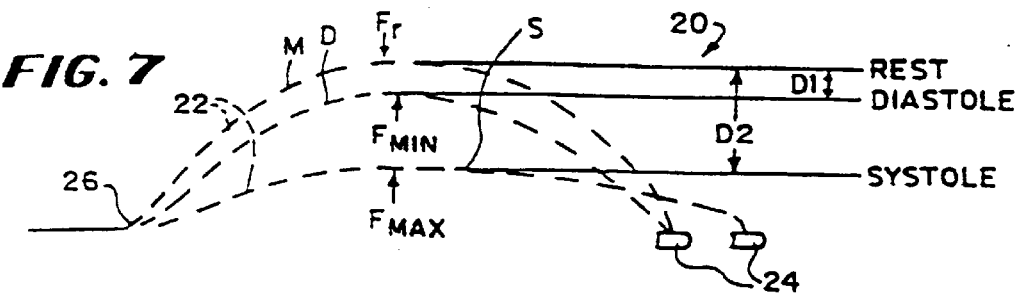
FIG. 7 is a side diagrammatic view of a spline for a multiple electrode structure in various at rest and radially deflected conditions.
Figure 8:
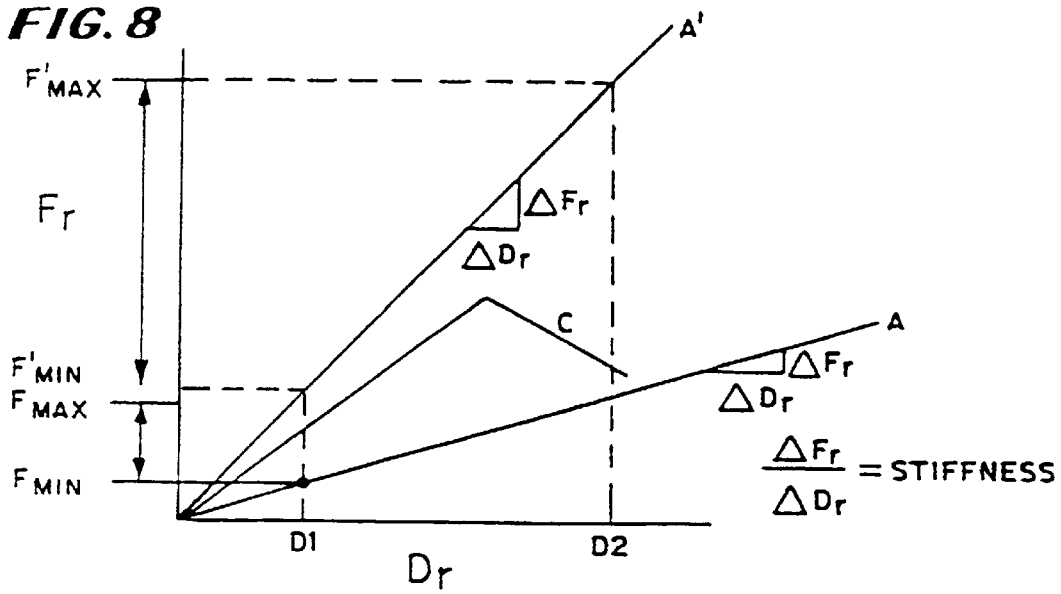
FIG. 8 is a graph plotting radial deflection against radial force for splines of different stiffnesses.

As FIG. 7 shows, the spline 22 can be normally biased toward an at rest position, which follows a maximum outwardly bowed contour, indicated by dotted contour line M in FIG. 7. At diastole, the spline 22 follows a different contour, indicated by dotted contour line D in FIG. 7, separated by radial distance $D_1$ from contour line M in FIG. 7. There is a radial force $F_r$ required to deflect the spline 22 by $D_1$, and a resulting reaction force $F_{MIN}$. The magnitude of $F_{MIN}$ corresponds to the minimum contact force that the spine 22 exerts against tissue during at diastole.

At systole, the spline 22 follows a still different contour, indicated by dotted contour line S in FIG. 7, separated by radial distance $D_2$ from contour line M in FIG. 7. There is a radial force $F_r$ required to deflect the spline 22 by $D_2$ and a resulting reaction force $F_{MAX}$. The magnitude of $F_{MAX}$ corresponds to the maximum contact force that the spine 22 exerts against tissue during at systole.

Assuming general uniformity in the dimensions of a human heart among the population, the deflection distance between $D_1$ (diastole) and $D_2$ (systole) can be considered to be approximately the same. The difference between $F_{MIN}$ and $F_{MAX}$ for this deflection distance ($D_2-D_1$) thus depends directly upon the radial stiffness function $S_r$.

Radial forces $F_r$ can be plotted as a function of radial deflections $D_r$ (see FIG. 8) for any spline 22. The slope of the resulting plot is the radial stiffness function $S_r$. For example, in FIG. 8, $F_{MIN}$ and $F_{MAX}$ for spline A are each less than $F'_{MIN}$ and $F'_{MAX}$ for spline A'. The difference between $F'_{MIN}$ and $F'_{MAX}$ for spline A is also greater than the difference between $F_{MIN}$ and $F_{MAX}$ for spline A'. The function $S_r$ for spline A is less than for spline A', which means that spline A' is radially stiffer than spline A.

Discontinuities or nonlinear regions associated with a given $S_r$ function (see plot C in FIG. 8) indicate that the spline 22 has buckled or has otherwise failed to uniformly deflect in response to radial force.

The spline radial force function $S_r$ can determined (see FIG. 9) by placing a structure 20 in a cylinder 124 which presses against and restrains all but the one selected spline 22, which projects through a window 126 in the cylinder 124. A pin 128 applies force perpendicular to the mid portion of the selected spline 22. A transducer 130 coupled to the pin 128 measures the force $F_r$ exerted against the spline 22 at successive points of radial deflection $D_r$ from the normal, outwardly biased, rest position of the spline 22 (which corresponds to contour line M in FIG. 7).

The function $S_r$ is expressed in terms of units of force (for example, in grams) per unit of deflection (for example, in inches). Lower values of $S_r$ indicate lower radial stiffness values and indicate a better ability to deform and create intimate contact along the contour of the endocardium without damage to tissue.

b. Spline Lateral Stiffness Function $S_l$

The spline lateral stiffness function $S_l$ expresses the ratio between lateral force ($F_l$) applied to the spline 22 in a circumferential direction normal to the plane of curvature and the lateral distance ($D_l$) the spline 22 deflects from its normal rest position in response to the lateral force. That is:

$$S_l = \frac{F_l}{D_l}$$

As with $S_r$, lateral forces $F_l$ can be plotted as a function of lateral deflections $D_l$ for any spline 22. The slope of the resulting plot is the lateral stiffness function $S_l$. Discontinuities or nonlinear regions associated with a given $S_l$ function indicate that the spline 22 has buckled or has otherwise failed to uniformly deflect in response to lateral forces.

Figure 9:
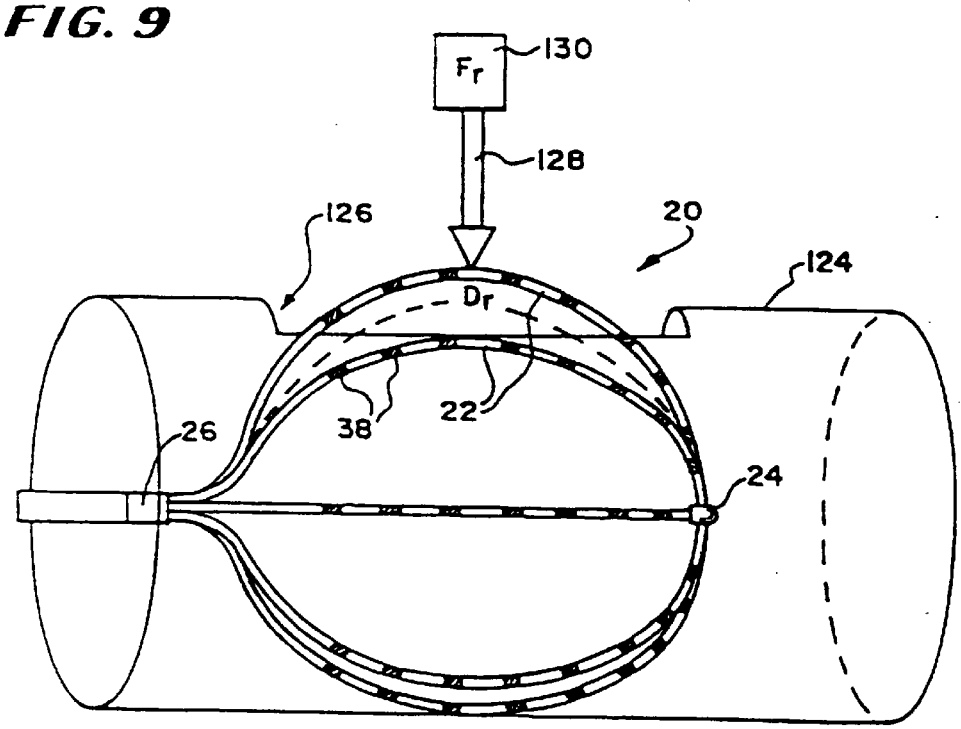
FIG. 9 is a diagrammatic view of the measurement of the radial stiffness function for a given spline.

The spline lateral force function $S_l$ can determined (see FIG. 10) by placing a structure 20 in the same cylinder 124 shown in FIG. 9, with the one selected spline 22 allowed to project through the window 126 in its normal rest condition. A pin 132 applies lateral force $F_l$ parallel to the axis of the structure 20 against the mid portion of the spline 22 to deflect the spline 22 fifteen degrees in opposite directions from its normal rest condition. A transducer 134 coupled to the pin 132 measures the force $F_l$ exerted against the spline 22 to deflect it at successive points of lateral deflection $D_l$ from the normal rest condition.

The function $S_l$ is expressed in terms of units of force (for example, in grams) per unit of lateral deflection from the rest condition (in degrees). Lower values of $S_l$ indicate lower lateral stiffness values. Lower values of $S_l$ indicate a better ability to deform and slide about surface structures on the endocardium without damage or trauma to tissue.

2. Spline Assembly Characteristics a. Torsional Stiffness Function $T_t$

Figure 11:
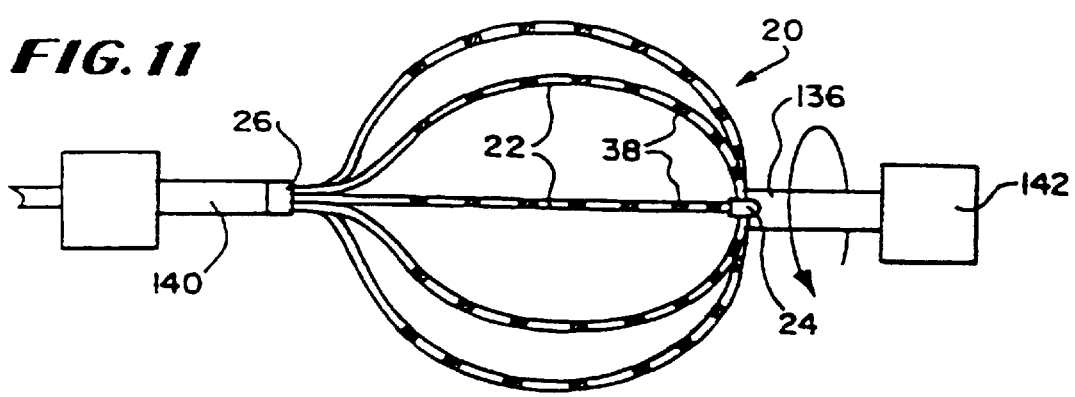
FIG. 11 is a diagrammatic view of the measurement of the torsional stiffness function for a given multiple electrode structure.

The torque function $T_t$ is determined (see FIG. 11) by holding the distal tip 24 of the structure 20 in a grip 136 that is free to rotate about the axis of the structure 20. A motorized shaft 140 rotates the base 26 about its normal rest condition. A transducer 142 coupled to the grip 136 senses angular deflection of the distal tip 24. Measurements of torque applied by the shaft 140 versus twist angle of the distal tip 24 are made.

Preferably, the shaft 140 rotates the base 26 through about fifteen degrees of rotation from the normal rest position. Fifteen degrees match the maximum anticipated twist of the ventricle during systole.

The transducer 142 measures the torque that must be applied to the distal tip 24 of the structure 20 to generate the angular deflection of the distal tip 24 with respect to the base 26 by the shaft 140 from the normal rest condition. The function $T_t$ is expressed in terms of the torsion of the distal tip 24 of the structure 20 (in inch-ounces) per unit of angular deflection of the tip 241 with respect to the base 26 of the structure 20 (in degrees).

Lower values of $T_t$ indicate greater compliance of the structure 20 to torsional movement of the heart. Lower values of $T_t$ characterize a better ability of the structure 20 to deform and hold its position during systole without trauma and damage to the heart or without motion artifacts arising from relative motion between the splines 22 and endocardium.

b. Tissue Force Function $T_f$

When the distal tip 48 of the structure 20 contacts tissue, it will transmit a contact force $F_c$ to the tissue. Contact force $F_c$ at the distal region of the structure 20 can occur as a result of progressive axial "creep" of the structure 20 toward the apex of the heart (in the ventricle) or toward the atrial appendage (in the atrium) during the cardiac cycle. Contact force $F_c$ can also occur as the physician remotely positions the structure 20 in the heart. The contact force $F_c$ can, if large enough, lead to trauma.

The magnitude of the contact force $F_c$ at any point in time depends upon:

(i) the diameter of the structure 20 at the time, which will, in turn, depend upon the size of the heart chamber and whether the cardiac cycle is in systole or diastole.

(ii) the amount by which the distal tip 24 is displaced along the axis of the structure 20 due to the contact.

(iii) the inherent mechanical stiffness of the structure 20.

The tissue force function $T_f$ expresses, for a given diameter of the structure 20, the ratio between contact force ($F_c$) at the distal tip 24 of the structure 20 and the axial distance ($D_a$) the distal tip 24 of the structure 20 is displaced by the contact force. That is:

$$T_f = \frac{F_c}{D_a}$$

Just as $S_r$ is the measure of the radial stiffness of a given spline 22, $T_f$ is a measure of the axial stiffness of the overall structure 20.

The tissue force function $T_f$ can determined (see FIG. 12) by placing a structure 20 in an open ended cylinder 144 having a predetermined interior diameter. The cylinder 144 imposes upon the structure 20 a particular diameter, just as would the walls of a heart chamber. A pin 146 enters the cylinder and applies force against the distal tip 24, displacing it along the axis of the structure 20 out of its rest position. A transducer 148 coupled to the pin 146 measures the force exerted against the distal tip 24 at successive points of axial displacement from its rest position.

Figure 12:
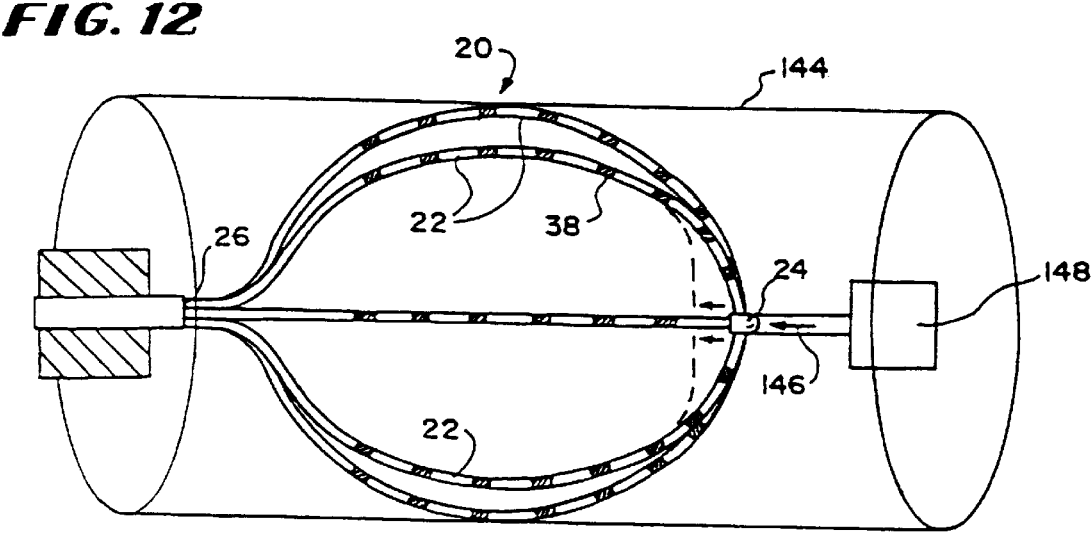
FIG. 12 is a diagrammatic view of the measurement of the axial stiffness function for a given multiple electrode structure.

Preferably, $T_f$ is calculated at different structure diameters. $T_f$ is measured when the structure 20 is radially unconstrained, i.e., without placement in a cylinder 144. $T_f$ is again measured with the structure 20 radially constrained within different cylinders 144, as shown in FIG. 12, having different interior diameters. The different cylinder diameters are selected to generally correspond to the expected diameter of a normal heart when in diastole (about 1.5 inches), when in systole (about 1.0 inch), and when between diastole and systole (about 1.25 inches).

The $T_f$ function can be plotted for each imposed structure diameter, with points interpolated between measured values. Discontinuities or nonlinear regions associated with a given $T_f$ function indicate that the structure 20 has buckled or warped, or has otherwise become unstable in response to axial force.

The function $T_f$ is expressed in terms of units of force (for example, in grams) per unit of axial deflection from the rest position (in inches). Lower values of $T_f$ characterize a better ability of the distal tip of the structure 20 to make conforming contact against tissue without inflicting trauma.

c. Tissue Pressure Function $T_p$

The tissue pressure function $T_p$ correlates distal tip contact force $F_c$ to the surface area of contact $A_{TIP}$ between tissue and the distal tip. $T_p$ expressed as follows:

$$T_p = \frac{F_c}{A_{TIP}}$$

where $F_c$ is the measured contact force at the distal tip of the structure 20, and $A_{TIP}$ is the surface area of contact between the distal tip of the structure 20 and tissue when $F_c$ is measured.

The quantity $T_p$ is a determinant of tissue trauma. Trauma caused by contact force exerted on small, localized area can be mediated by distributing the same contact force over a larger contact area, thereby reducing contact pressure.

The tissue pressure function $T_p$ can be determined (see FIG. 13) by placing a structure 20 in an open ended cylinder 144, like the one shown in FIG. 12. The cylinder 144 has a predetermined interior diameter at diastolic or systolic dimensions, or somewhere in between. The distal tip 24 of the structure 20 is allowed to project from the open end of the cylinder 144.

The base of structure 20 is attached to a fixture 150, which suspends the structure 20 within the cylinder 144 over a work surface 152. The work surface 152 carries animal endocardial tissue 154. A shaft 156 incrementally drives the fixture 150 toward the work surface 152.

As the shaft 156 lowers the distal tip 24 incrementally into contact with the tissue 154, a transducer 158 successively measures contact force $F_c$ created between the distal tip 24 and the tissue 154. The surface area of the distal tip $A_{TIP}$ contacting the tissue 154 is also measured at successive increments of contact force $F_c$. $T_p$ is thereby derived at successive increments of contact force $F_c$ and surface area $A_{TIP}$.

Figure 15:
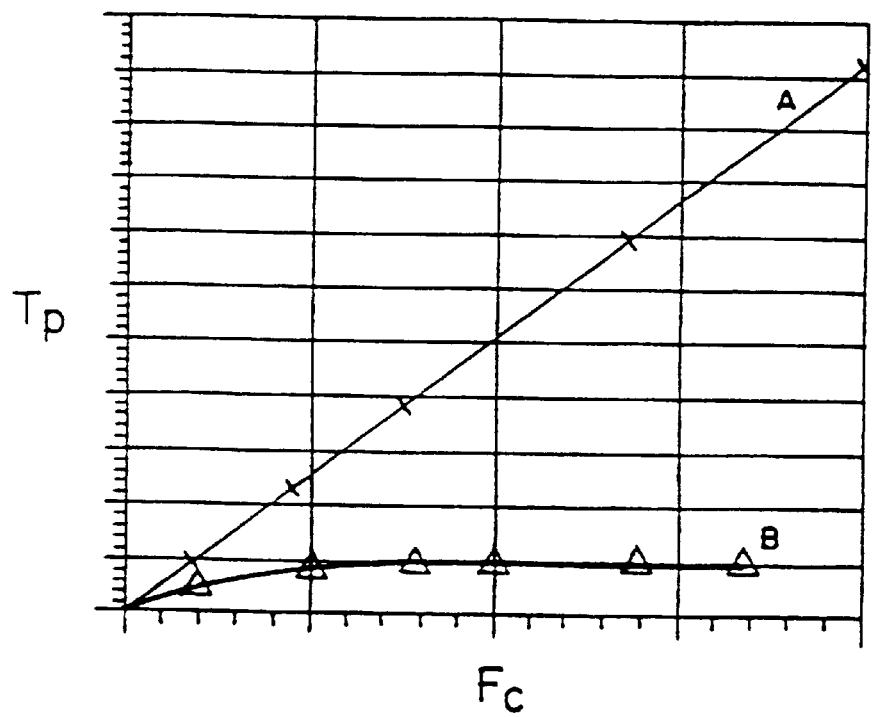
FIG. 15 is a representative graph that plots tissue pressure as a function of contact force for a spline.

Tissue pressure $T_p$ can be plotted with respect to contact force $F_c$, as FIG. 15 shows. The value of the pressure function directly determines the degree of tissue trauma that can be anticipated arising from increasing distal contact with tissue.

Figure 14:
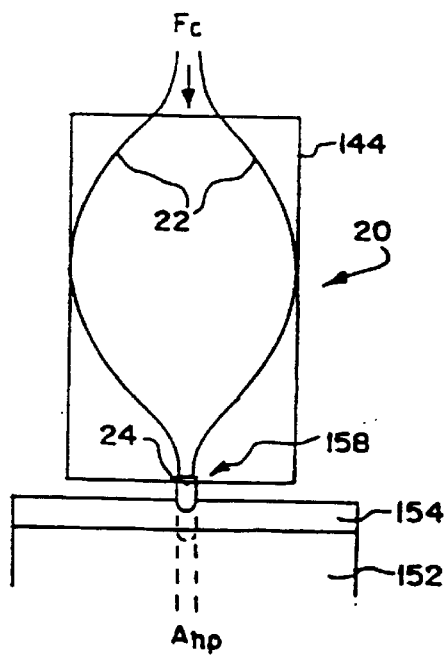
FIG. 14 is a diagrammatic view of the measurement of the tissue pressure function for a preferred multiple electrode structure whose distal area of tissue contact remains constant with increasing contact force.

Plot A in FIG. 15 shows a steep, essentially constant slope, with $T_p$ increasing in a linear fashion with increasing $F_c$. Plot A is associated with a distal tip structure 158 like that shown in FIG. 14. When tested in the manner just described, the structure 158 presents a stiff point of contact with tissue 154. As FIG. 14 shows, the surface area of the contact $A_{TIP}$ does not significantly change as $F_c$ changes. As the contact force $F_c$ increases, localized tissue pressure at the point of contact increases in a linear fashion. The steep, unchanging slope of Plot A in FIG. 15 is characteristic of the distal tip structure 158, which, with increasing contact force $F_c$, creates increasing localized pressure on tissue. Use of the tip structure 158 could lead to trauma, protrusion, and, worst, perforation of tissue.

On the other hand, Plot B in FIG. 15 shows a more shallow slope that decreases in a nonlinear fashion with $T_p$. Plot B approaches a constant value despite increasing $F_c$. Plot B is characteristic of a distal tip structure 160 like that shown in FIG. 13. The distal tip structure 160 presents a flexible point of contact with tissue. The flexure of the structure 160 causes the surface area of the contact to increase with increasing $F_c$. The increasing contact force is distributed by the structure 160 over an increasing tissue surface area. The structure 160 tends to stabilize tissue pressure at lower levels, thereby diminishing the risk of tissue trauma, protrusion, and perforation.

3. Spline Geometry Characteristics a. Spline Components

Figure 16:
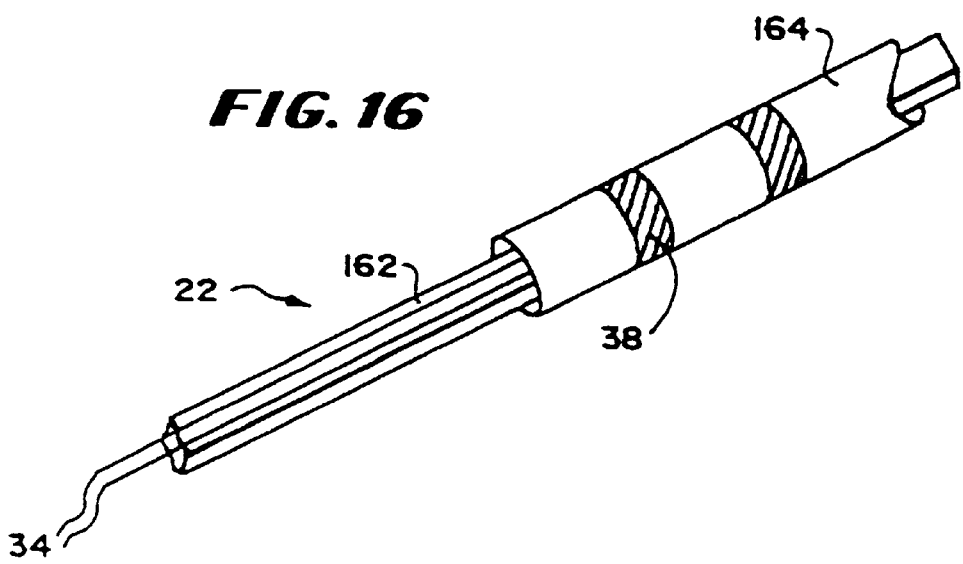
FIG. 16 is an assembly view of a composite spline structure showing the various components that affect the mechanical properties of the spline.

As FIG. 16 shows, a spline 22 typically is a composite structure comprising a flexible core body 162 made from resilient, inert wire or plastic, a surrounding sleeve of plastic tubing 164, and associated electrodes 38 and signal wires 34. Of these components, the individual mechanical characteristics of the core body 162 and the tubing 164 most contribute to the overall mechanical characteristics of the composite spline 22.

A low degree of stiffness can be achieved using resilient, inert wire, like nickel titanium (commercially available as Nitinol material) for the core body 162. Resilient injection molded inert plastic or stainless steel can also be used. As will be discussed later, the wire preferably has a rectilinear cross section to provide differentiation between radial stiffness and torsional stiffness. A preferred range of rectilinear thicknesses is from about 0.004 inch to 0.008 inch. A preferred range of rectilinear widths is from about 0.010 inch to about 0.020 inch.

Materials under load undergo two types of deformation—elastic and plastic. Elastic deformation is a change in shape that is completely recoverable once the deforming loads are removed. Plastic deformation is a change in shape that results in a permanent residual change in shape once the deforming loads are removed. Most ductile materials will exhibit elastic deformation at low levels of stress, followed by plastic deformation at higher levels of stress. The stress level that distinguishes the two regimes is known as the yield strength. Yield strength is typically defined as the amount of stress that produces the acceptable low value of about 0.2% permanent deformation (strain) once the stress is removed.

A core body 162 also must provide a high degree of elastic deformation, as contrasted with plastic deformation. The body 162 must also provide a high degree of rebound. The degree of rebound expresses the ability of the body 162 to uniformly return to the same rest condition after removal of the deflection force (either radial or torsional). A high degree of rebound is a favorable bio-mechanical characteristic for a spline, because it provides a structure with uniform and predictable function.

The added presence of the sleeve of plastic tubing 164 adds to the overall stiffness and reduces the rebound of the spline 22 as a function of the elasticity of the plastic material, its diameter, and wall thickness.

For example, the stiffness and rebound of a composite spline 22 made of a nickel titanium core body 162 enclosed within an elastic polyurethane plastic sleeve 164 (35D durometer) with an outside diameter of about 0.028 inch and a wall thickness of 0.002 inch, exhibits approximately 110% of the inherent stiffness and approximately 90% of the elastic rebound of the core body 162 alone. On the other hand, by using a sleeve 164 with greater stiffness (for example, a comparatively inelastic Pebax material) with an increased outside diameter (approximately 0.036 inch), the stiffness of the composite spline 22 is approximately about 200% that of the inherent stiffness and only about 50% of the elastic rebound of the core body 162 alone.

Preferably, the stiffness and rebound characteristics of the core body 162 should dominate the bio-mechanical properties of the composite assembly of the spline 22. To achieve this objective, the tubing 164 should be selected from materials having an inherent low degree of stiffness and high elasticity, like polyurethane. Furthermore, the wall thickness and outside diameter of the tubing should be minimized to maximize flexibility and rebound for the composite assembly of the spline 22.

b. Spline Cross Section Geometry

The cross section geometry of a spline 22 affects its mechanical characteristics.

A cylindrical cross section presents isotropic stiffness. In optimizing function of a cylindrical spline 22, $S_r$ and $S_l$ must be balanced against each other.

A rectilinear cross section, on the other hand (as FIG. 16 shows), presents anisotropic stiffness. The spline radial stiffness function $S_r$ for a rectilinear spline 22 will not have the same characteristics as the spline lateral stiffness function $S_l$. A rectilinear spline 22 can exhibit a lesser degree of stiffness to bending in response to a radial force, than to lateral deflection in response to a lateral force.

Through the selection of cross section geometry, it is possible to differentiate among bio-mechanical functions and to independently optimize functions. For example, through the use of rectilinear splines 22, a desirable degree of both radial flexibility and lateral stiffness can be achieved. For this reason, rectilinear spline geometry is preferred.

The width of the splines 22 affects the number of splines 22 that the structure 20 can accommodate, particularly when collapsed. By reducing the width of individual splines 22, the collapsible structure 20 can accommodate more splines 22. Since the circumferential spacing of the splines 22 is least near the distal tip 24, the splines 22 can be locally thinned in this region, when desired, to present a compact geometry that accommodates the collapsing of multiple, closely spaced splines 22.

The thickness of the splines 22 affects flexibility and the magnitude of the stress developed during flexing. Thinning the splines 22 imparts greater flexibility, while at the same time reducing the magnitude of the stress developed during flexing. Since greatest stress upon flexing occurs near the distal tip (where the greatest degree of bending occurs), the splines 22 can be locally thinned in this region, when desired, to impart greater resistance to stress failure.

The localized reductions of width and/or thickness also reduces force required to collapse the structure 20.

c. Spline Axial Geometry

Figure 17:
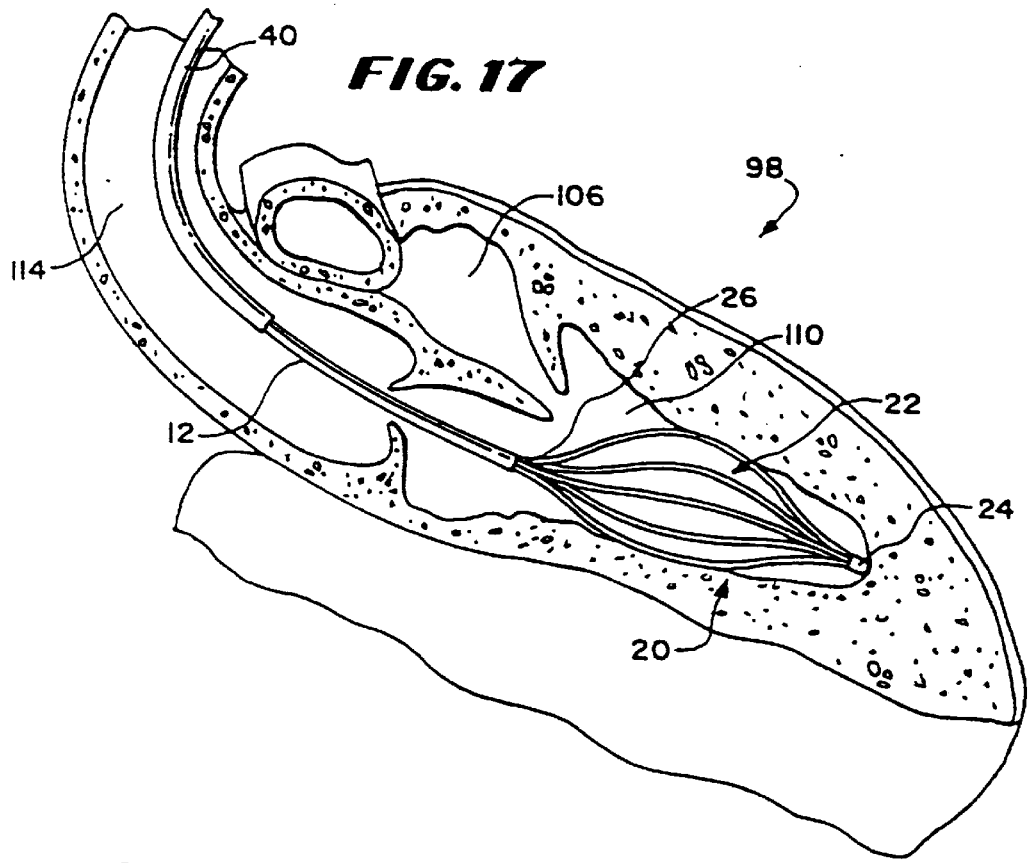
FIG. 17 is a diagrammatic section of the interior of the right side of the human heart at diastole with an unstable multiple electrode structure deployed.
Figure 18:
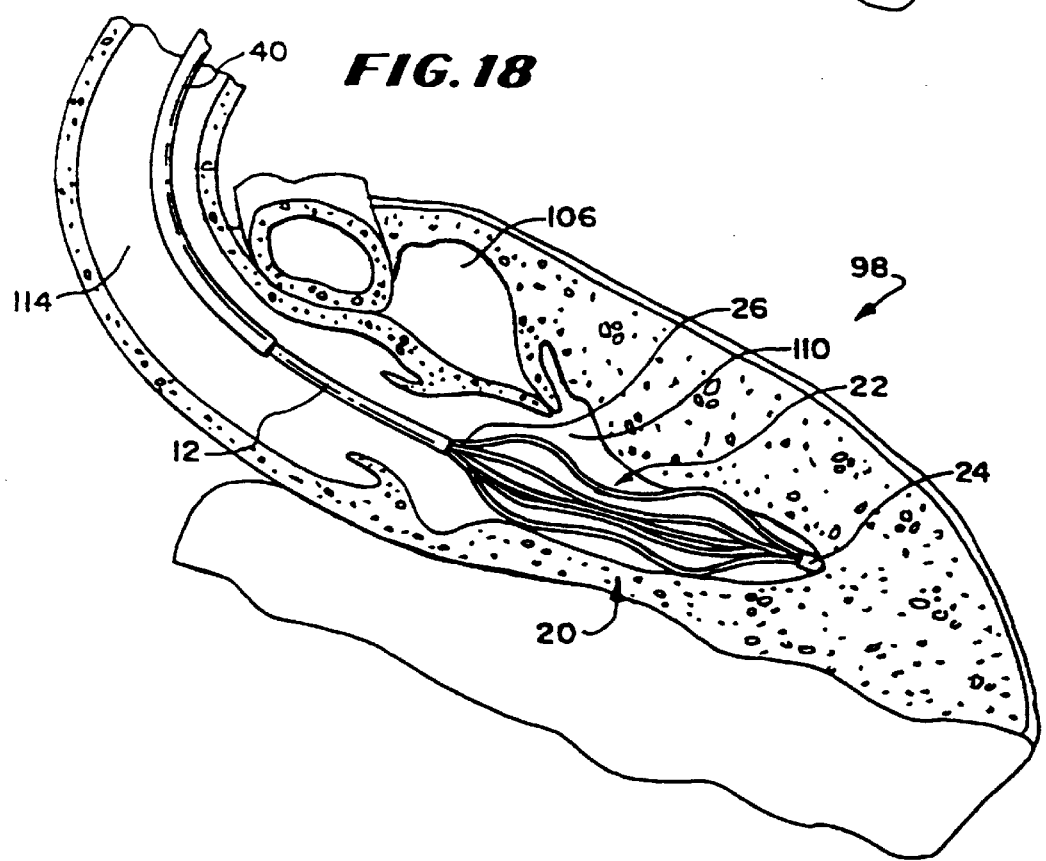
FIG. 18 is a diagrammatic section of the interior of the right side of the human heart at diastole with an unstable multiple electrode structure deployed, showing buckling and warping of the splines due to the mechanical instability of the structure.

The overall geometry of splines 22 as constrained between the distal tip 24 and base 26 of the structure 20 directly effects the ability of the structure to maintain stable contact with the endocardium during systole. If the structure 20 is not stable (as FIGS. 17 and 18 show), the structure 20 will not deform uniformly, but will be observed to buckle and warp during systole, as FIG. 18 shows. The biomechanical functions $S_r$ and $T_f$ will exhibit discontinuities and nonlinear regions, also indicating the instability of the structure.

As FIG. 18 shows, the splines 22 in an unstable structure will, upon buckling, shift or lose contact with the endocardium. This creates motion artifacts, signal distortion, and mapping inaccuracies. Furthermore, as the distal tip 24 loses its ability to move axially in concert with the splines 22, tissue contact with electrodes near the distal tip 24 of the splines 22 will be lost, too.

The instability of a given structure 20 during inwards radial movement of the splines 22 can also cause the splines 22 to abrate or scrape the endocardium and structures on the endocardium.

C. Unstable Spline Geometry

Figure 19:
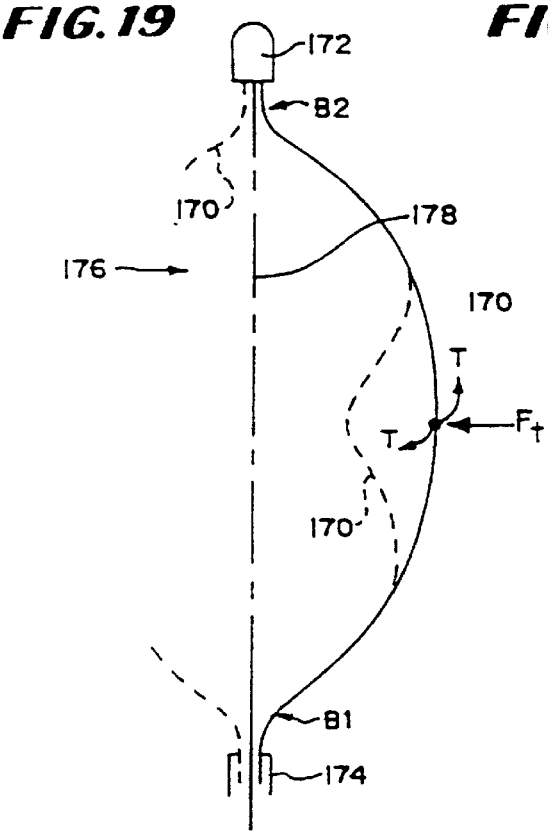
FIG. 19 is a diagrammatic side view of the axial geometry of a spline in an unstable multiple electrode support structure, showing the effects of the application of a radial force at the mid portion of the spline.

FIG. 19 shows splines 170 constrained between a distal tip 172 and a base 174 in a way that creates a structure 176 having an unstable axial geometry, which will buckle during systole in the manner shown in FIG. 18. The constraint of structure 170 creates a first complex bend Bi near the base 174, as the splines 170 extend from the base 174 along the axis 178 of the structure 176 and then bend outwards. The constraint shown in FIG. 19 also creates a second complex bend B2 near the distal tip 172, as the distal ends of the splines 170 are brought back along the axis 178 of the structure 176 for gathering within the distal tip 172. The distal ends of the spline 170 are typically firmly fixed by epoxy and swaging within the distal tip 172. This structure 176 is exemplified by the multiple electrode basket structure described in U.S. Pat. No. 5,411,025.

The axial geometry of the structure 176 is unstable in several respects. The application of a radial force $F_r$ upon the mid-section of a spline 170 creates torsional instability. Suspended between two complex bends B1 and B2, the spline 170 will be observed to react to a radial force by twirling in an unpredictable fashion side-to-side about the structure axis 178, as arrows T in FIG. 19 show. The continued application of the radial force $F_r$ and the continued twirling of the spline 170 also creates radial instability. Subjected to both uncontrolled radial and torsional forces, the spline 170 both buckles and warps in the manner shown in phantom lines in FIG. 19. FIG. 18 also shows the buckle and warp of the splines typical of this structure 176 during systole.

Figure 21:
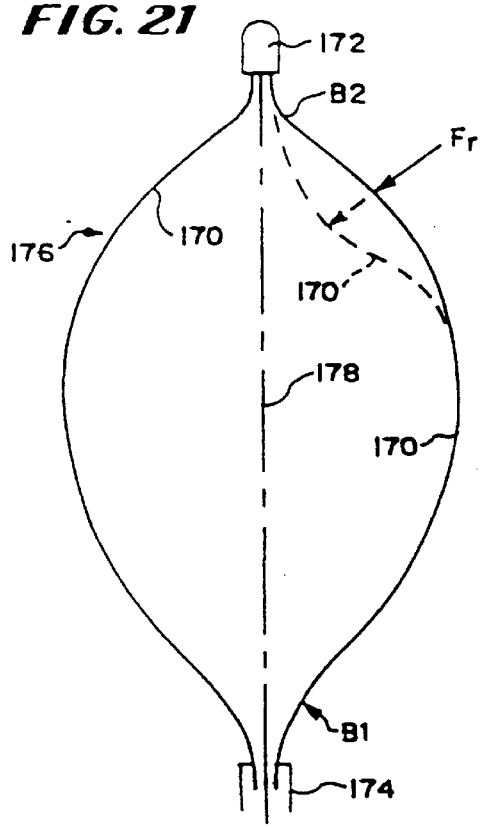
FIG. 21 is a diagrammatic side view of the axial geometry of a spline in the unstable multiple electrode support structure shown in FIG. 19, showing effects of the application of a radial force above the mid portion of the spline.

Furthermore, as FIG. 21 shows, the application of a radial force $F_r$ above the mid-section of a spline 170 in the structure 176 pulls a significant portion of the spline 170 away from tissue contact. This is because the second complex bend B2 does not resist downward movement of the spline 170 away from the distal tip 172. In fact, the presence of the complex bend B2 promotes downward movement in response to a radial force above the spline mid portion.

D. Stable Spline Geometry

Figure 20:
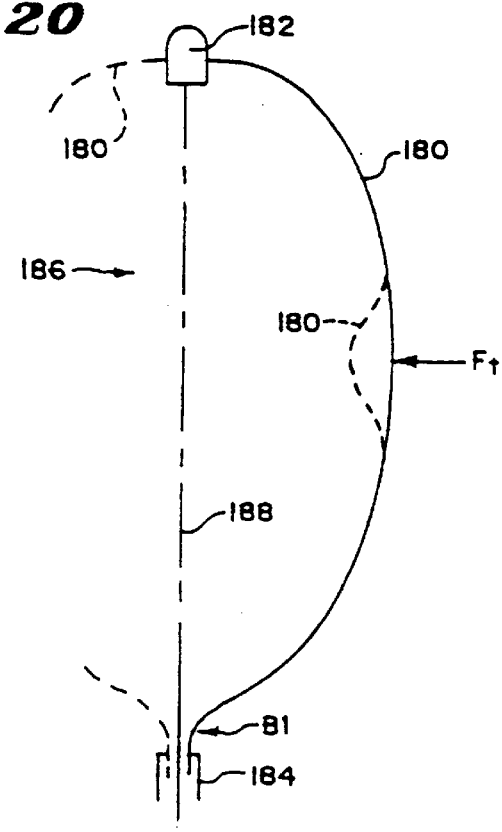
FIG. 20 is a diagrammatic side view of the axial geometry of a spline in a preferred stable multiple electrode support structure, showing the effects of the application of a radial force at the mid portion of the spline.

FIG. 20 shows splines 180 constrained between a distal tip 182 and a base 184 in a way that creates a structure 186 having a stable axial geometry. The constraint of the structure 186, like that shown in FIG. 19, creates a first complex bend B1 near the base 184, as the splines 1130 extend from the base 184 along the axis 188 of the structure 186 and then bend outwards. Unlike FIG. 19, the constraint shown in FIG. 20 does not create a second complex bend near the distal tip 182. Instead, the splines 170 enter the distal tip 182 generally perpendicular to the axis 188 of the structure 186.

This structure 186 is exemplified by the multiple electrode basket structure described in copending patent application Ser. No. 08/206,414, filed Mar. 4, 1994 and entitled "Multiple Electrode Support Structures," which is incorporated herein by reference.

Figure 23:
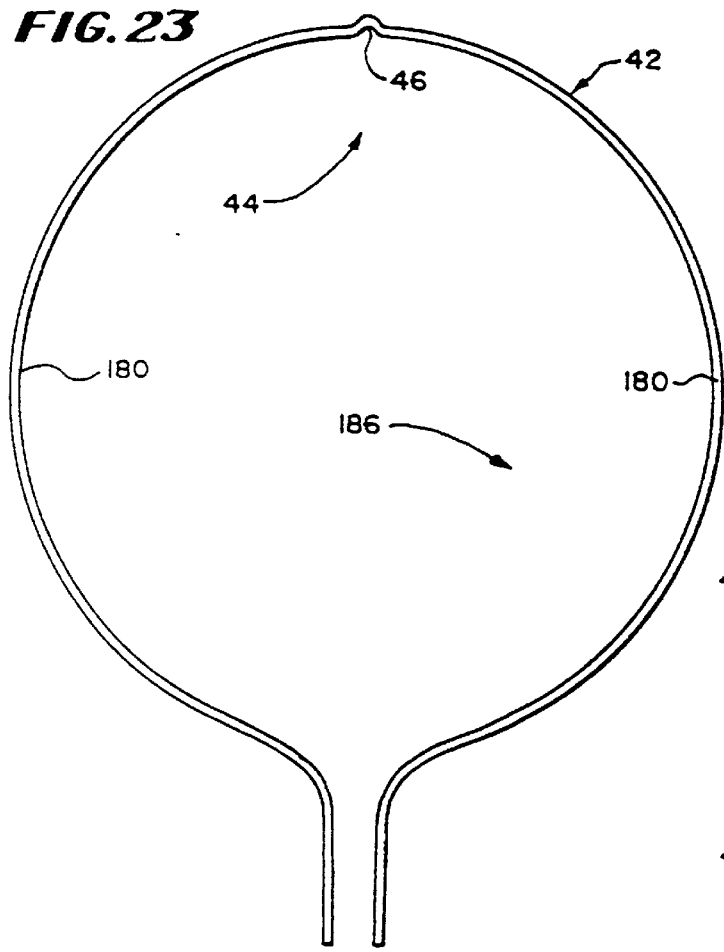
FIG. 23 is an elevation view of an integral, hoop-like body that can be assembled to form an electrode support assembly that embodies the features of the invention.

FIGS. 23 to 33 show further details of the preferred stable geometry of the structure 186. As FIG. 23 shows, two spline elements 180 are paired together in an integral body 42. Two or more spline bodies 180 are joined together to form the structure 186, as FIG. 30 shows.

Figure 24:
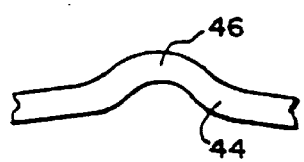
FIG. 24 is an enlarged view of the mid-section of the hoop-like body shown in FIG. 23, showing the detent used to lock the body into an associated end cap.

Each body 42 includes a mid-section 44 from which the spline elements 180 extend as an opposed pair of legs. In this arrangement, the body 42 is generally shaped like a hoop (see FIG. 23). As FIGS. 23 and 24 show, the mid-section 44 includes a preformed detent, whose function will be described later.

The hoop-like body 42 is preferably made from the resilient, inert wire, like nickel titanium described above. As also described above, the body 42 preferably has a rectilinear cross section.

Figure 25:
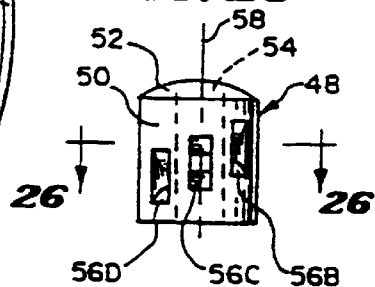
FIG. 25 is a side elevation view of the end cap used to assemble the hoop-like body shown in FIG. 23 into an electrode support assembly.
Figure 26:
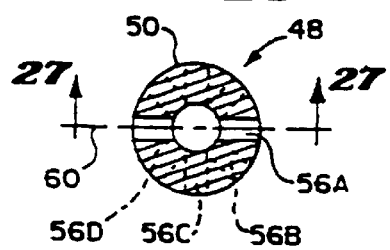
FIG. 26 is a top section view of the end cap taken generally along line 26—26 in FIG. 25.
Figure 27:
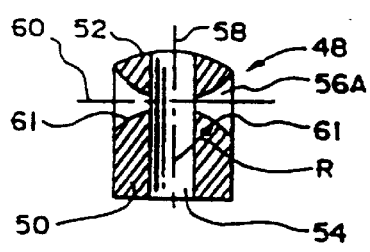
FIG. 27 is a side section view of the end cap taken generally along lines 27—27 in FIG. 26.

In this embodiment, the distal tip 182 comprises an end cap 48 (see FIG. 30). As FIGS. 25 to 27 show, the end cap 48 has a generally cylindrical side wall 50 and a rounded end wall 52. A longitudinal bore 54 extends through center the cap 48.

Slots 56A; 56B; 56C; and 56D extend through the cap 48 diametrically across the center bore 54. The number of slots can vary. In the illustrated embodiment, there are four through-slots 56A–D.

The slots 56A–D are circumferentially spaced about the axis 58 of the bore 54. The axis 60 of each slot 56A–D extends diametrically through the center axis 58 (see FIGS. 26 and 27), passing through the center bore 54.

The slot axes 60 are also spaced longitudinally along the bore axis 54. The resulting staggered pattern of slots 56A–D is both circumferentially and longitudinally spaced along each 180° segment of the hub 48 (see FIGS. 29 and 30). As FIG. 30 best shows, slot 56A is closest to the end wall 52. The slot 56D is farthest from the end wall 52. Intermediately slots 56B and 56C are sequentially spaced in between the slots 56A and 56D.

In the illustrated and preferred embodiment, the cap 48 is made of an inert, machined metal, like stainless steel. The bore 54 and slots 56A–D are preferably formed by conventional EDM techniques. Still, inert molded plastic materials can be used to form the cap 48 and associated openings.

A spline leg 180 of the hoop-like body 42 can be inserted through a slot 56A–D until the mid-body section 44 enters the bore 54. The detent 46 snaps into the bore 54 to lock the body 42 to the end cap 48, with the opposed pair of spline legs 180 on the body 42 radiating free of the respective slot 56A–D. Sequentially inserting the four hoop-like bodies 42 in the four slots 56A–D orients and locks the spline elements 180 in the radiating pattern shown in FIG. 30. The three dimension support assembly 20 shown in FIG. 30, having an axial geometry shown in FIG. 20, results.

This arrangement creates a "soft" constraint at the distal tip 182. The mid-body section 44 is not epoxied or swaged or otherwise firmly fixed within the slot 56. Rather it is constrained by the detent 46 only against sliding out of the distal tip 182. Slight rotational motion of the spline 180 within the tip 182 is permitted, because of the small amount of lateral clearance between the spline and the distal tip bore 54. This is in contrast to the "hard" constraint shown in FIG. 19, where the distal ends of the splines 170 are rigidly glued or mechanically swaged into a fixed location within the distal tip 172, thereby prevented from moving within the distal tip 172.

The absence of rigid, immovable constraint within the distal tip 182 also adds to the effective beam length of the spline 180 at the distal tip 182. This, in turn, reduces stress and fatigue.

Figure 28:
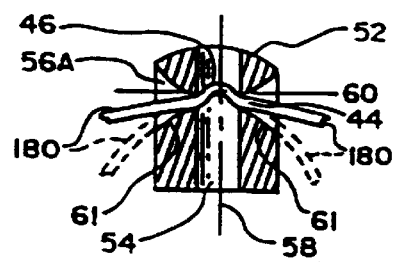
FIG. 28 is a side section view showing the mid-section of a hoop-like body shown in FIG. 24 locked in place within the end cap shown in FIG. 25.

In the illustrated and preferred embodiment, the lower surface 61 of the end cap slots 56 is curved (see FIGS. 27 and 28). The curved lower surface 61 contacts the spline elements 180 (see FIG. 28) when they are bent, or deflected, a prescribed amount. The curvature of the lower slot surface is selected to lend positive support to the spline elements 180 when bent this amount, as FIG. 28 shows. The positive support of the surface 61 prevents spline deflection beyond a minimum bend radius. The bend radius is selected to be above that which failure-mode stresses are most likely to develop in the spline elements 180.

In the illustrated embodiment, failure mode stresses are most likely to occur when the slidable sheath 40 compresses and collapses the spline elements 180. The preservation of a minimum bend radius that the cap 48 furnishes prevents sharp bends and failure-mode stresses from developing when the spline elements 180 are collapsed into their most stressed position.

The specific minimum bend radius selected depends upon the material from which the spline elements 180 are made and the thickness of the spline elements 180. In the preferred embodiment, which uses Nitinol spline elements 180 with a thickness of about 0.007", the minimum bend radius imposed by the surface 61(shown as radius R in FIG. 7) is about 0.025".

In the support assembly 20, the base 184 includes an anchor member 62 and a mating lock ring 64 (see FIGS. 30 to 33). The anchor member 62 fits with an interference friction fit into the distal end 16 of the catheter tube 12. The lock ring 64 includes a series of circumferentially spaced grooves 66 into which the free ends of the spline legs 180 fit. The lock ring 64 fits about the anchor member 62 to capture with an interference fit the free ends of the spline legs 180 between the interior surface of the grooves 66 and the outer surface of the anchor member 62 (see FIG. 33).

The anchor member 62/lock ring 64 assembly holds the spline elements 180 radially spaced while their preformed shape holds them in a desired flexed condition.

The hoop-like body 42, slotted end cap 48, and anchor member 62/lock ring 64 assembly provide manufacturing efficiencies, as the number of the components parts required to form the support assembly 186 is minimized. The slotted cap 48 circumferentially aligns and stabilizes the spline elements 180, both circumferentially and longitudinally. The sequential insert and snap lock process of the attaching the bodies 42 to the slotted cap 48 also significantly simplifies the assembly process.

The axial geometry of the structure 186 shown in FIGS. 20 and 30 is stable in several respects. As FIG. 20 shows, the application of a radial force $F_r$ upon the mid-section of a spline 180 does not create torsional instability. The spline 180 is suspended at the base 184 along the axis 188 of the structure 186 and at the distal tip 182 crosswise to the axis 188. Stabilized in this manner, the spline 180 reacts to a radial force by radial deflection, and not by twirling side-to-side about the structure axis 188. Subjected to complex forces, the spline 180 nonetheless deflects in a controlled, consistent fashion, without buckling or warping, as the phantom lines in FIG. 20 show.

Figure 22:
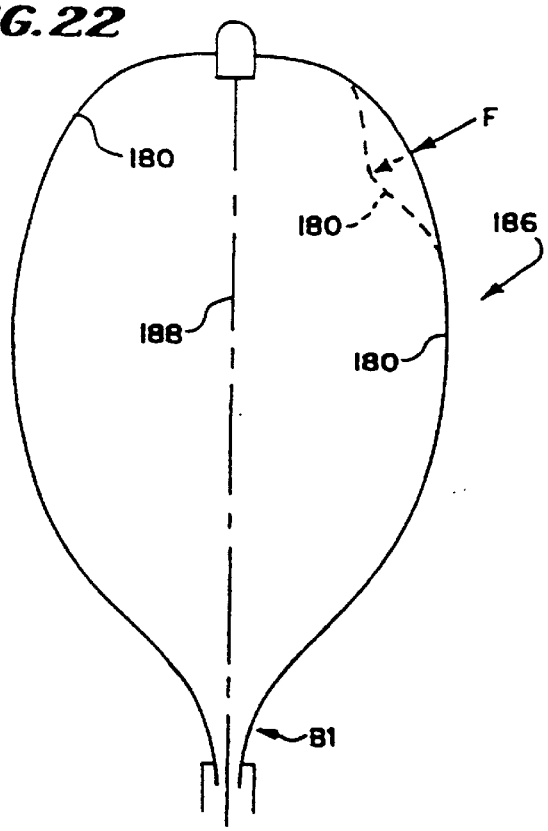
FIG. 22 is a diagrammatic side view of the axial geometry of a spline in the stable multiple electrode support structure shown in FIG. 20, showing effects of the application of a radial force above the mid portion of the spline.

Furthermore, as FIG. 22 shows, the application of a radial force $F_r$ upon above the mid-section of a spline 180 causes localize radial deflection and does not does not pull the entire length of spline 180 away from tissue contact. This is because the perpendicular connection of the spline 180 to the distal tip 182 actively resists downward movement of the spline 180 away from the distal tip 182. Unlike the unstable structure 176 shown in FIGS. 20 and 21, there is no complex bend B2 near the distal tip 182 to promote downward movement in response to a radial force above the spline mid portion.

The following Example further demonstrates that, when judged in terms of the bio-mechanical functions described above, a structure 186 made in accordance with the preferred embodiment is superior to a structure 176 constructed generally in accordance with the teachings of U.S. Pat. No. 5,411,025.

EXAMPLE

A multiple electrode structure 186 was made according to the preferred embodiment as above described, and as shown in FIG. 1. The splines 180 were made from the preferred rectilinear Nickel Titanium core body 162 enclosed with thin walled tubing 164, as above described. The splines 180 achieved a low degree of stiffness with a high elastic deformation dominated by the inherent mechanical characteristics of the nickel titanium core body 162. Constrained between the base 184 and distal tip 182 in the manner shown in FIG. 30, the splines 180 normally assumed the outwardly bowed stable geometry shown in FIG. 20. The normal outwardly bowed geometry had an oversized diameter of about 1.88 inches, which is larger than a heart chamber diameter during diastole (about 1.5 inches). The minimum tissue contact force $F_{MIN}$ is created by radial force of the endocardium upon the "preloaded" splines, reducing the oversized diameter during diastole.

Figure 34:
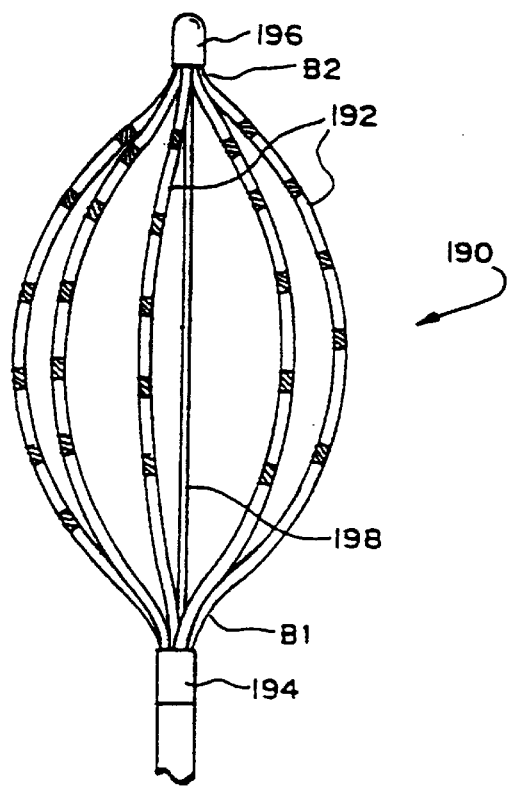
FIG. 34 is a perspective view of a multiple electrode support structure that embodies the unstable axial geometry shown in FIGS. 19 and 21.

This structure 186 was compared to a commercially available multiple electrode basket structure 190 made by Cordis-Webster, as shown in FIG. 34. The structure 190 appears to have been made in accordance with the teachings of U.S. Pat. No. 5,411,025. The structure 190 comprised five splines 192 constrained between a base 194 and a distal tip 196. The splines 192 were made from using a core body (believed to be nickel titanium with a hemispherical cross section) surrounded by tubing having an outside diameter of about 0.036 inch.

The structure 190 incorporates the unstable axial geometry shown in FIG. 19, and described above. Constrained between the base 194 and tip 196, the splines 192 displayed the two complex bends B1 and B2.

The splines 192 of the structure 190 exhibited a lower degree of elasticity than the structure 186. Constrained between the base 194 and distal tip 196, the splines 192 assumed an outwardly bowed configuration with an undersized diameter of about 1.1 inches, which is smaller than a heart chamber diameter during diastole. To further enlarge the diameter of the splines 192, the structure 190 included an axially movable pull wire 198 extending through the base 194 and attached to the distal tip 196. By pulling rearwards on the wire 198, the splines 192 deflected further outwards, increasing the diameter of the structure. In this way, the structure 190 created the minimum tissue contact force $F_{MIN}$ during diastole.

1. Comparing Spline Radial Stiffness Functions $S_r$

The radial stiffness functions $S_r$ for the preferred structure 186 and the other structure 190 were derived according to the methodology earlier described (shown in FIG. 9). A cylinder having an interior diameter of 1.44 inches constrained each structure while radial force was applied to individual splines.

Figure 35:
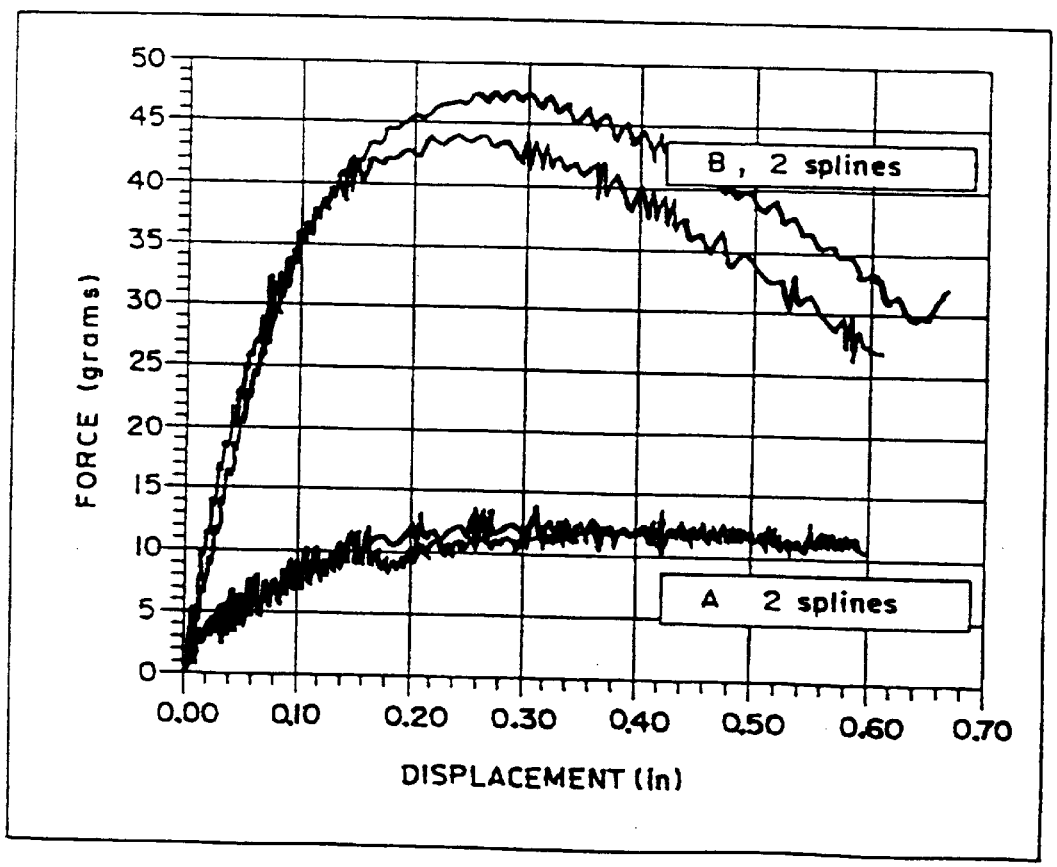
FIG. 35 is a graph comparing the radial stiffness functions of splines in the preferred structure shown in FIG. 30 and the other structure shown in FIG. 34.

FIG. 35 shows the radial stiffness function plot for the preferred structure 186 (two splines) (Curves A) and the radial stiffness function plot for the other structure 190 (two splines) (Curves B). Curves A and B demonstrate the significant differences between the two radial stiffness functions, both in terms of magnitude and in terms or shape.

In terms of magnitude, the slope of the radial stiffness function of Curve A (for the preferred structure 186) is about 60 gram/inch. In contrast, the slope of the radial stiffness function of Curve B (for the other structure 190) is about 320 gram/inch. The radial stiffness function Curve A thereby demonstrates the significantly lower "stiffness" of the spline 180 of the preferred structure, compared to the higher "stiffness" of the spline 192 of the other structure 190 (radial stiffness function Curve B).

In terms of shape, Curve A is seen to rise and then level off, indicating that the maximum radial force $F_{MAX}$ during systole (i.e., during increasing radial force) is, in effect, self-limiting. In contrast, Curve B is seen to steeply rise throughout systole, indicating that the maximum force $F_{MAX}$ rises continuously.

The Curves A and B in FIG. 35 underscore the significantly different results obtained by achieving $F_{MIN}$ by over sizing (the preferred structure 186) versus by achieving $F_{MIN}$ through stiffness (the other structure 190). As before explained, the preferred structure 186 incorporates splines 180 with relatively low stiffness and high rebound. The preferred structure 186 oversize the structure diameter to achieve $F_{MIN}$ during diastole by radial force created by the endocardium.

In contrast, the other structure 190 incorporates splines 192 with relatively high stiffness and low rebound. The other structure 190 under sizes the structure diameter and uses the pull wire 198 to establish $F_{MIN}$, thereby actively bring the relatively stiff splines 192 into contact with the endocardium during diastole. FIG. 35 shows that, during systole, the relatively low stiffness splines 180 of the preferred structure 186 mediate $F_{MAX}$, as evidenced by the low, essentially constant maximum force value (Curve A). FIG. 35 shows that, during systole, the relatively high stiffness splines 192 of the other structure 190 exert significantly greater maximum force values (Curve B).

2. Comparing Spline Lateral Stiffness Functions $S_t$

Figure 10:
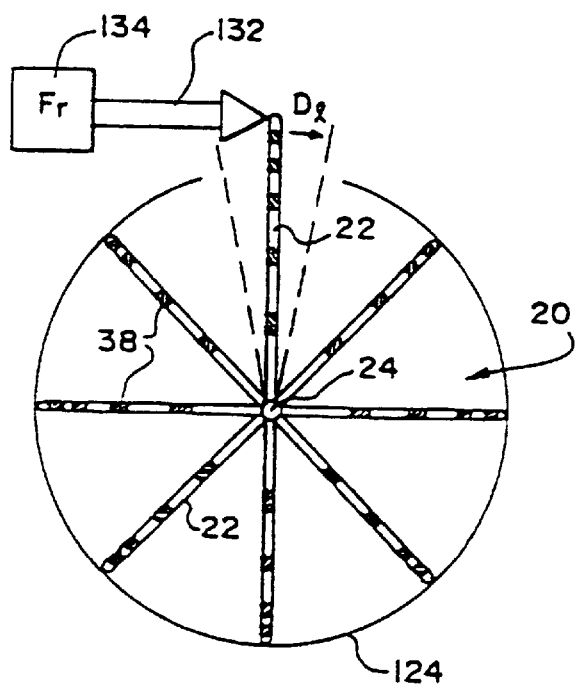
FIG. 10 is a diagrammatic view of the measurement of the torsional stiffness function for a given spline.

The lateral stiffness functions $S_t$ for the preferred structure 186 and the other structure 190 were derived according to the methodology earlier described (as FIG. 10 shows). A cylinder having an interior diameter of 1.44 inches constrained each structure while lateral force was applied to individual splines.

Figure 36:
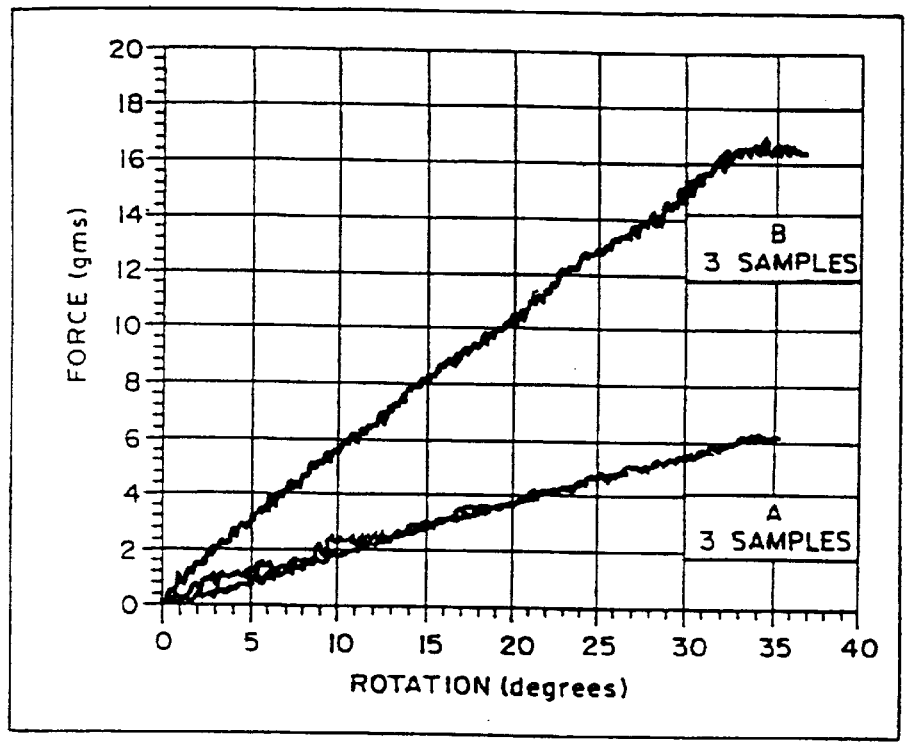
FIG. 36 is a graph comparing the torsional stiffness functions of spline in the preferred structure shown in FIG. 30 and the other structure shown in FIG. 34.

FIG. 36 shows the lateral stiffness function plot for the preferred structure 186 (for three splines) (Curve A) and the lateral stiffness function plot for the other structure 190 (for three splines) (Curve B). The lateral stiffness curves A and B demonstrate significant differences in, lateral stiffness of the two structures 186 and 190.

The lateral stiffness function curves A and B demonstrate that the splines 180 of the preferred structure 186 have significantly lower lateral stiffness than the splines 192 of the other structure 190. In terms of magnitude, the slope of the lateral stiffness function of Curve A (for the preferred structure 186) is about 0.19 gram/degree. In contrast, the slope of the lateral stiffness function of Curve B (for the other structure 190) is about 0.51 gram/degree.

3. Comparing Axial Stiffness Functions $T_f$

The axial stiffness functions $T_f$ for the preferred structure 186 and the other structure 130 were derived according to the methodology earlier described (as FIG. 12 shows). Cylinders having interior diameters of 1.44 inches (simulating diastole); 0.94 inch (simulated systole); and 1.19 inches (simulating between diastole and systole) constrained each structure 186 and 190 while axial force deflection was applied to the distal tips of the structures 186 and 190. During deflection, the axial stiffness function $T_f$ the other structure 190 was derived with the pull wire 198 taunt and with the pull wire 198 loose.

Figure 37:
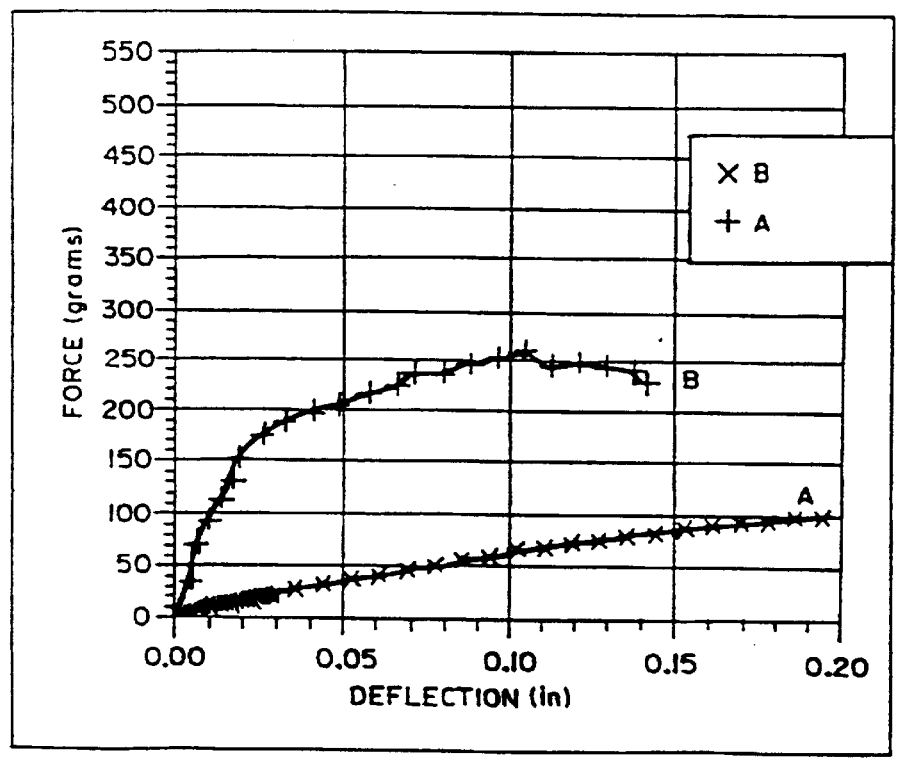
FIGS. 37 to 39 are graphs comparing the axial stiffness functions for the preferred structure shown in FIG. 30 and the other structure shown in FIG. 34 between diastole and systole.
Figure 38:
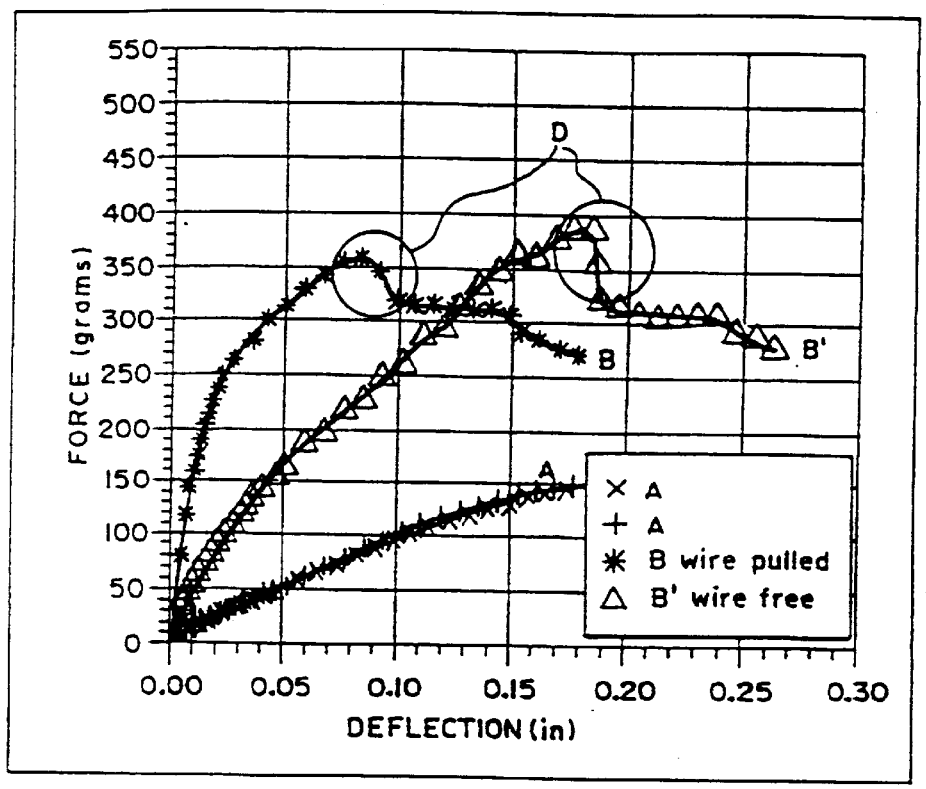
Figure 39:
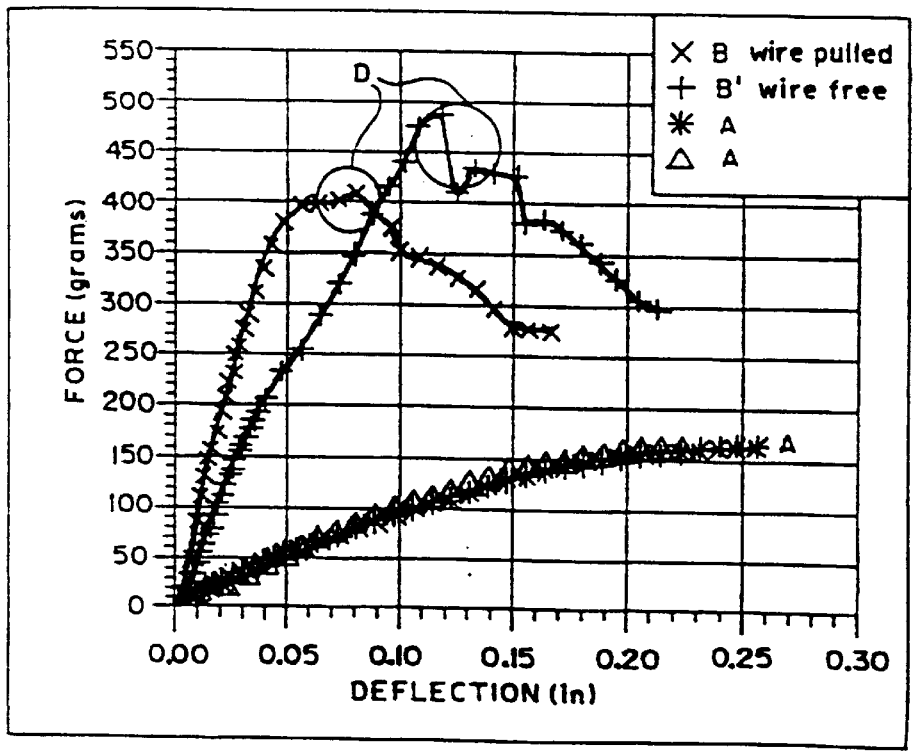

FIGS. 37; 38; and 39 show, respectively, at the diastolic diameter; the intermediate diameter; and the systolic diameter, the axial stiffness functions $T_f$ for the preferred structure 186 (Curve A, with two samples in FIGS. 38 and 39) and the other structure 190 (Curve B, with Curve B for taunt pull wire and Curve B' for loose pull wire in FIGS. 38 and 39).

Curves A and B/B' demonstrate the significant differences between the two axial stiffness functions, both in terms of magnitude and in terms of shape.

In terms of magnitude, the axial stiffness function Curve A demonstrates the significantly less axial stiffness of the preferred structure 186, compared to the axial stiffness of the other structure 190 (axial stiffness function Curves B/B').

In terms of shape, Curve A is seen to rise at a gradual slope. The gradual slope of $T_f$ indicates that incremental changes in deflection bring about relatively small, incremental changes in contact force $F_c$, even when the structure 186 is fully compressed at systole.

In contrast, Curves B/B' are seen to steeply rise (FIGS. 37 and 38) and then even more steeply rise (FIGS. 38 and 39). The steep slope of $T_f$ indicates that large increases in contact force $F_c$ occur with small increments in axial deflection, particularly during systole.

Curves B/B' are also seen to have discontinuities (indicated by regions D in FIGS. 38 and 39) marked by a sudden change in slope. These discontinuities determine that the other structure 190 will experience buckling or warping during axial deflection during systole, in the manner shown in FIG. 18. Curve A is free of such discontinuities, indicating a more stable structure, which will deform uniformly during systole in the manner shown in FIG. 6.

Figure 45:
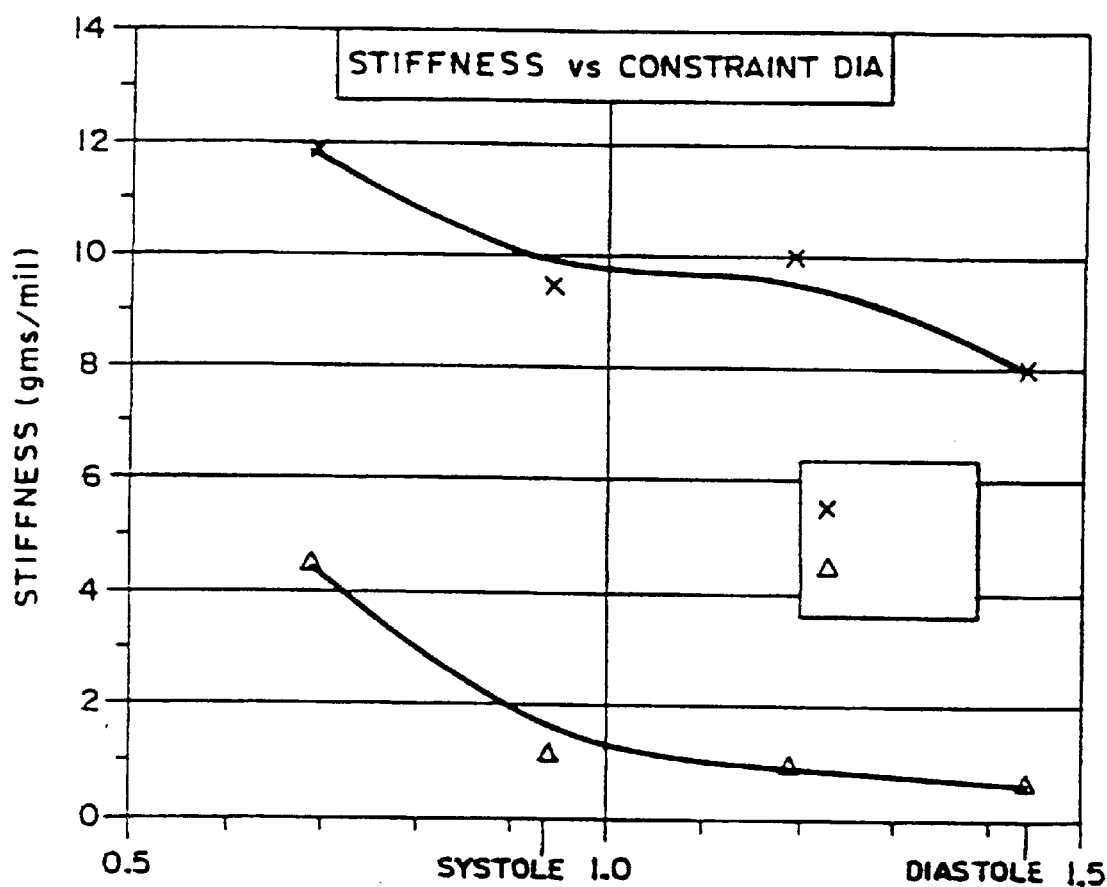
FIG. 45 is a plot of the stiffnesses versus constraint diameter for the preferred structure and the other structure.

The stiffness of each structure 186 and 190 is evaluated by measuring the slope of the axial stiffness curves A/B/B'. FIG. 44 shows a table tabulating the various slope (i.e. stiffness) values measured. FIG. 45 shows a compilation of curves plotting constraint diameter of the structures versus stiffness. FIG. 45 also generally indicates the constraint diameters corresponding to systole (0.94 in) and diastole (1.44 in). FIGS. 44 and 45 demonstrate that the stiffness of the preferred structure 186 ranges from ⅛th to 1/12th the stiffness of the other structure 190 over the expected range of systolic and diastolic heart diameters.

4. Comparing Tissue Pressure Functions $T_p$

Figure 13:
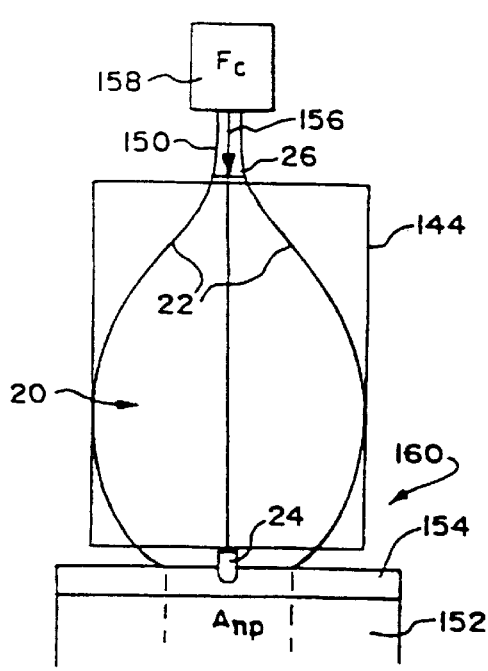
FIG. 13 is a diagrammatic view of the measurement of the tissue pressure function for a preferred multiple electrode structure whose distal area of tissue contact increases with increasing contact force.

The tissue pressure functions $T_p$ for the preferred structure 186 and the other structure 190 were derived according to the methodology earlier described (shown in FIG. 13).

Figure 40:
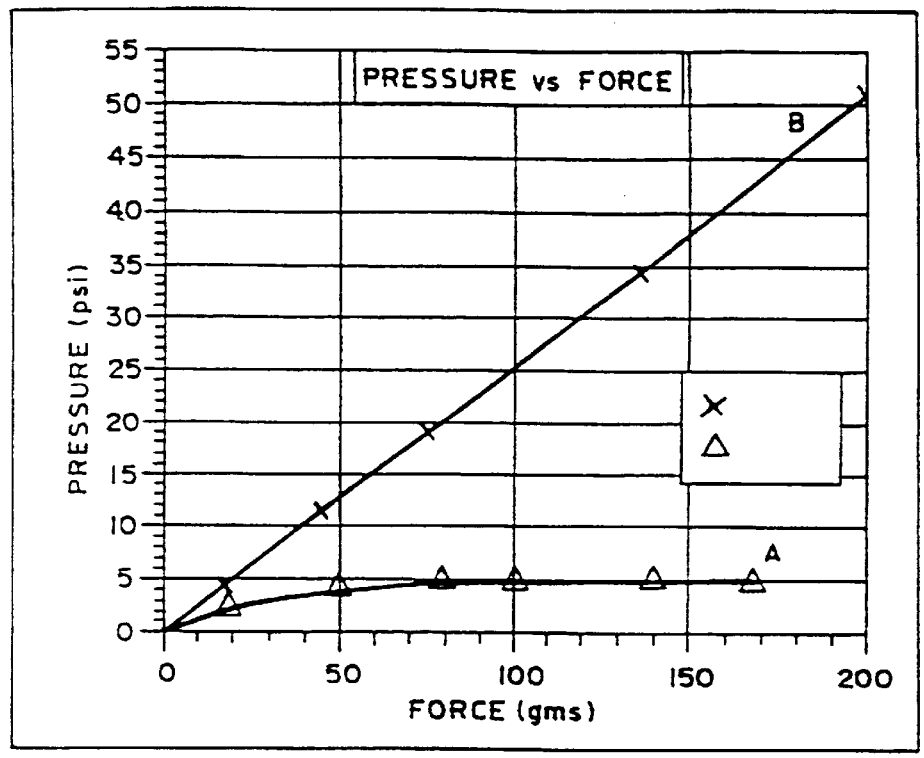
FIG. 40 is a graph comparing the distal tip pressure as a function of contact force for the preferred structure shown in FIG. 30 and the other structure shown in FIG. 34.

Tissue pressure $T_p$ was plotted as a function of contact force $F_c$ for the two structures, as FIG. 40 shows. In FIG. 40, Curve A shows the resulting plot for the preferred structure 186. Curve B shows the resulting plot for the other structure 190.

The plot for the preferred structure 186 (Curve A) shows tissue pressure $T_p$ rising gradually with increasing contact force $F_c$, then reaching a maximum level and thereafter remaining essentially constant, despite increasing contact force $F_c$. In sharp contrast, the plot for the other structure 186 (Curve B) shows tissue pressure $T_p$ continuously rising in a linear fashion with contact force $F_c$.

Experimental Verification of Contact Pressure Measurements

Figure 42A:
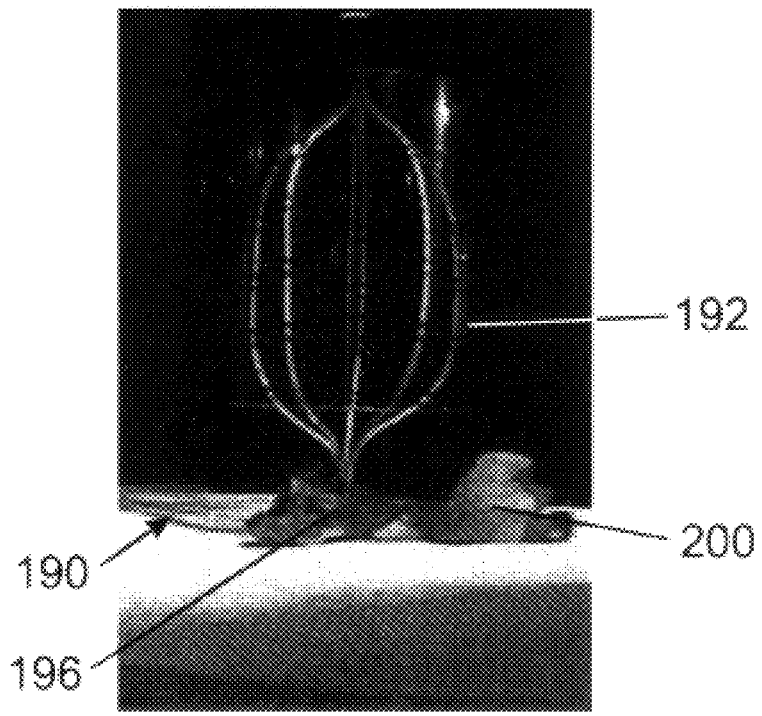
FIGS. 42A to 42E are photographs of the structure shown in FIG. 34 taken as contact force at the distal tip is increased while the distal tip is in contact with heart tissue.
Figure 42B:
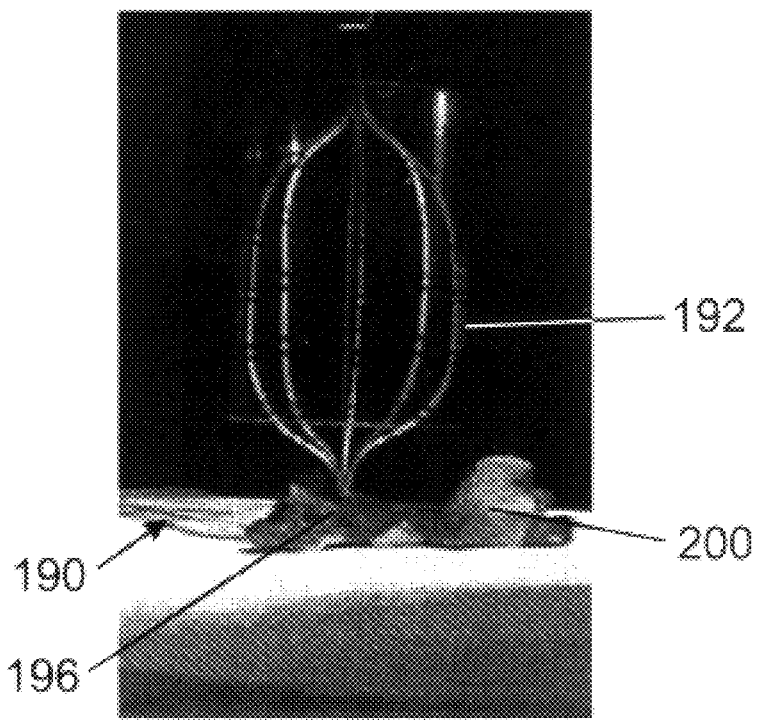
Figure 42C:
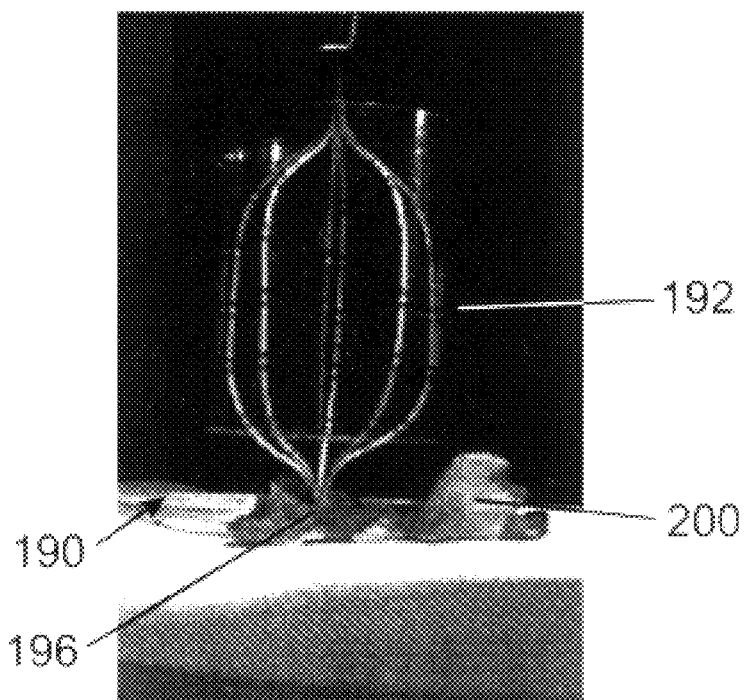
Figure 42D:
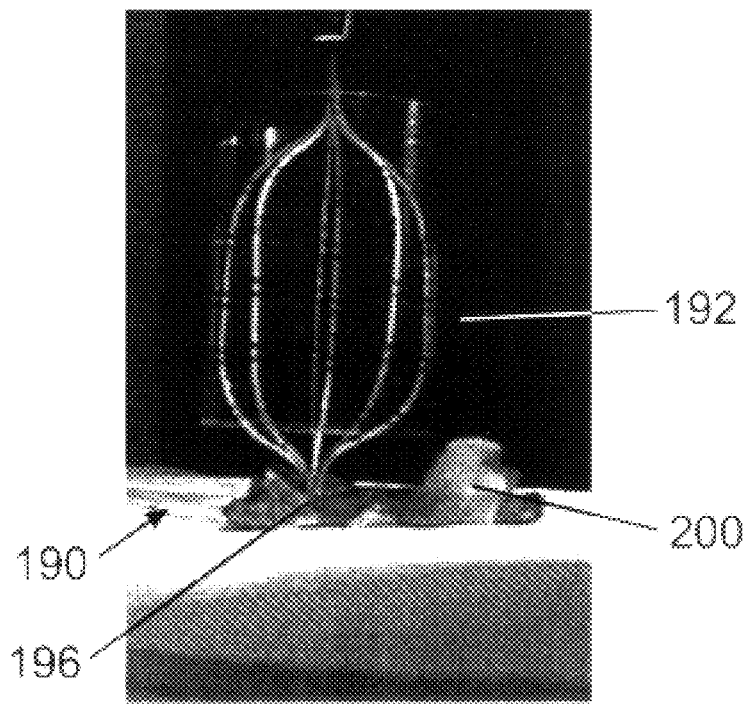
Figure 42E:
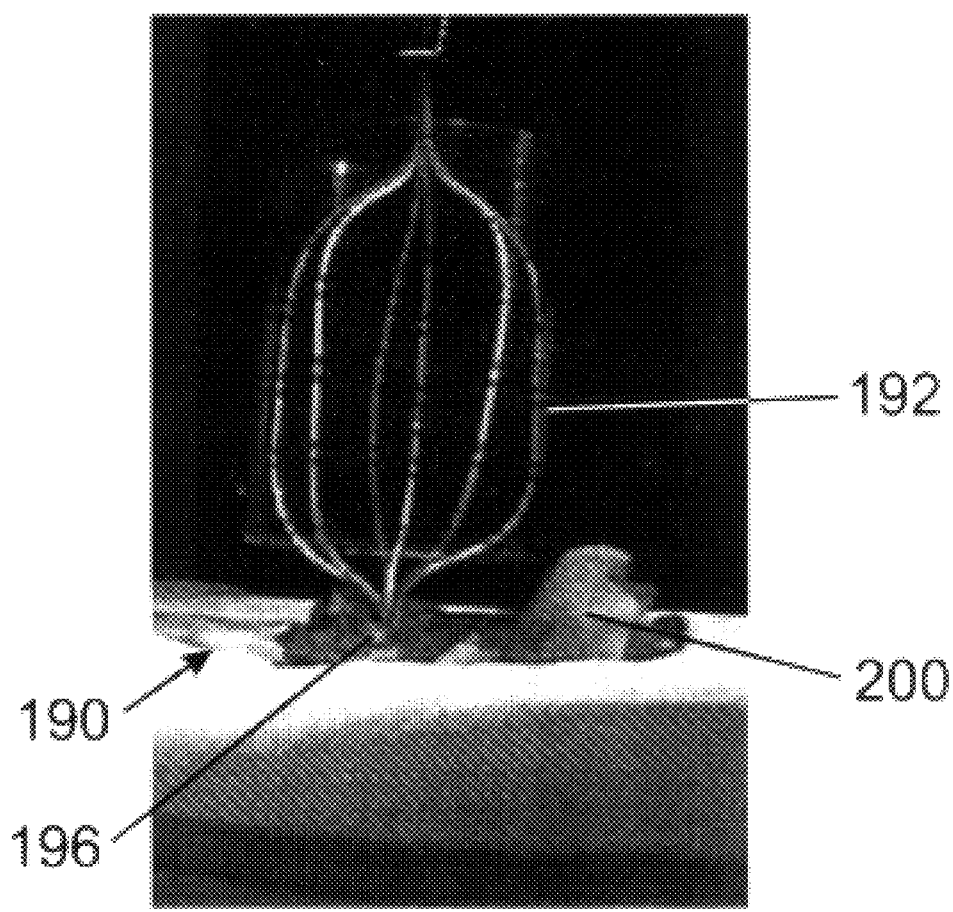

FIGS. 42A to 42E are successive photographs showing the other structure 190 during measurement of the tissue pressure function $T_p$. FIG. 42A shows the distal tip 196 applying a contact force $F_c$ of 18 grams to a section of endocardial tissue 200 (lamb atrial tissue). FIGS. 42B and 42C show the distal tip 196 applying increasing contact forces $F_c$ of 45 grams and 75 grams, respectively. FIGS. 42D and 42E show the distal tip 196 applying a still increasing contact force $F_c$ of 136 grams and 200 grams, respectively.

FIG. 42E demonstrates that continued application of the axial force causes the splines 192 of the other structure 190 to buckle and warp. The discontinuities D in the radial stiffness function $S_r$ (FIG. 35) and axial stiffness function $T_f$ (FIGS. 38 and 39) for the structure 190 indicated that this instability would occur.

FIGS. 42A to 42E show that, as the contact force $F_c$ increases, the surface area of the distal tip 196 of the other structure 190 remains constant. As the contact force $F_c$ increases, the distal tip 196 incrementally protrudes further into tissue 200 in "javelin-like" fashion, until the tip 196 is essentially buried in the tissue 200 (see FIGS. 42C/D/E).

FIGS. 42A to 42E also show that the complex curve configuration near the distal tip 196 of the other structure 190 holds the splines 192 surrounding the distal tip 196 away from contact with tissue 200.

Figure 43A:
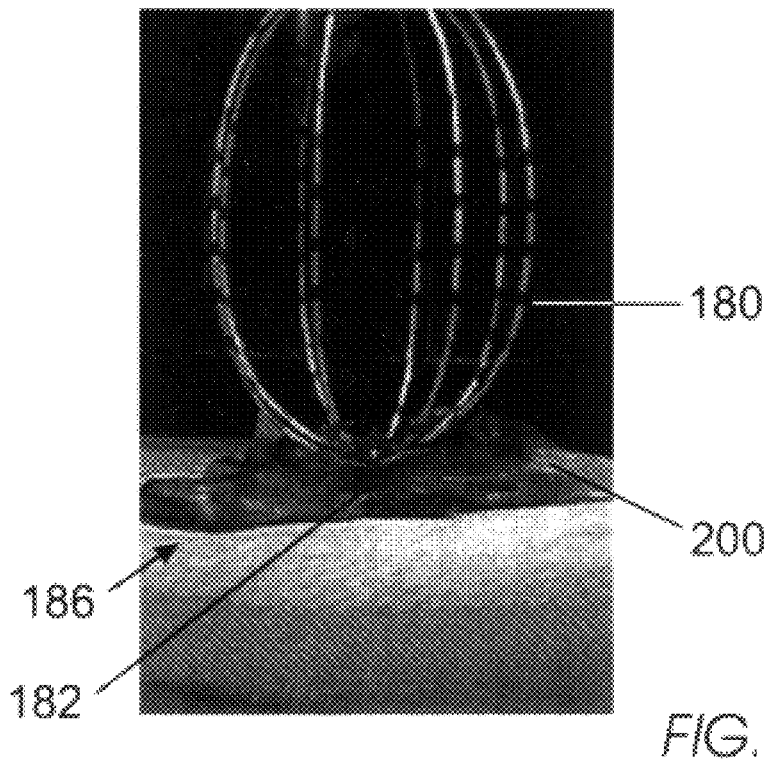
FIGS. 43A to 43E are photographs of the preferred structure shown in FIG. 30 taken as contact force at the distal tip is increased while the distal tip is in contact with heart tissue.
Figure 43B:
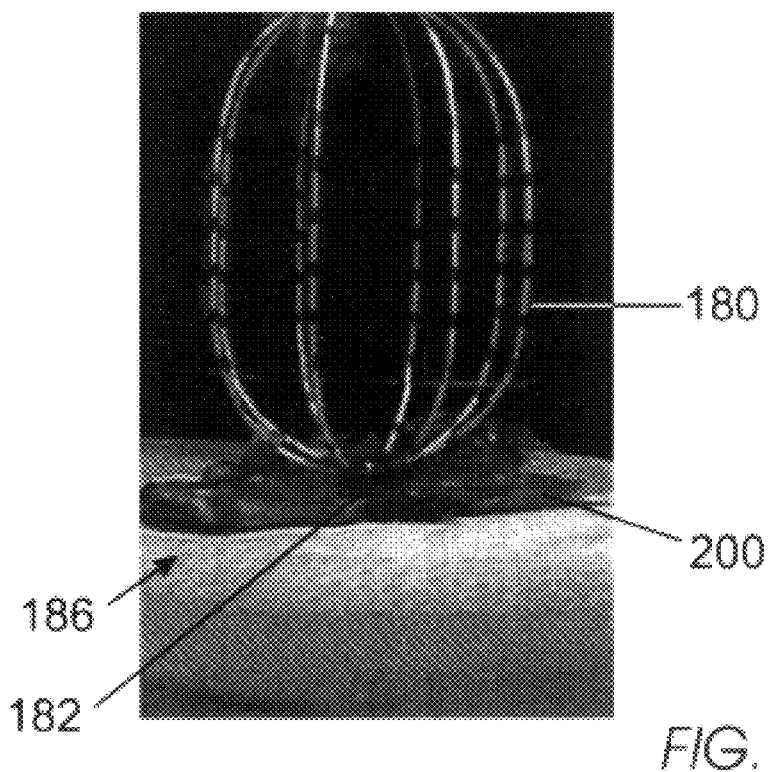
Figure 43C:
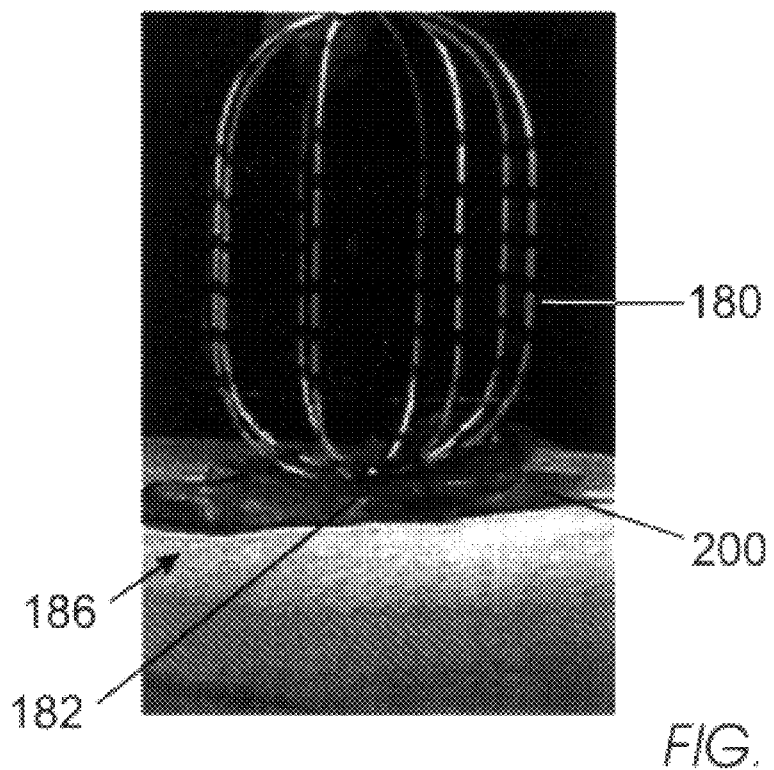
Figure 43D:
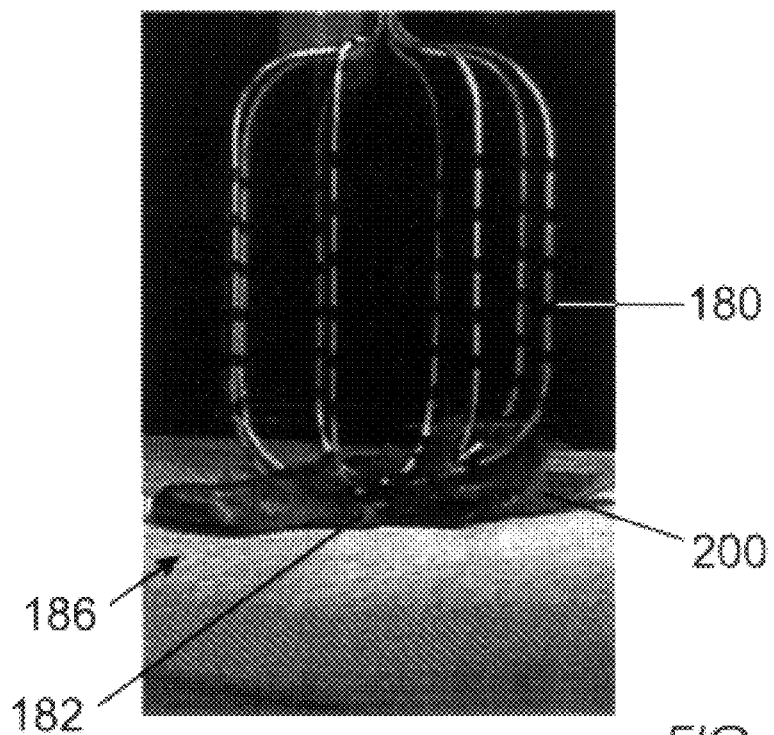
Figure 43E:
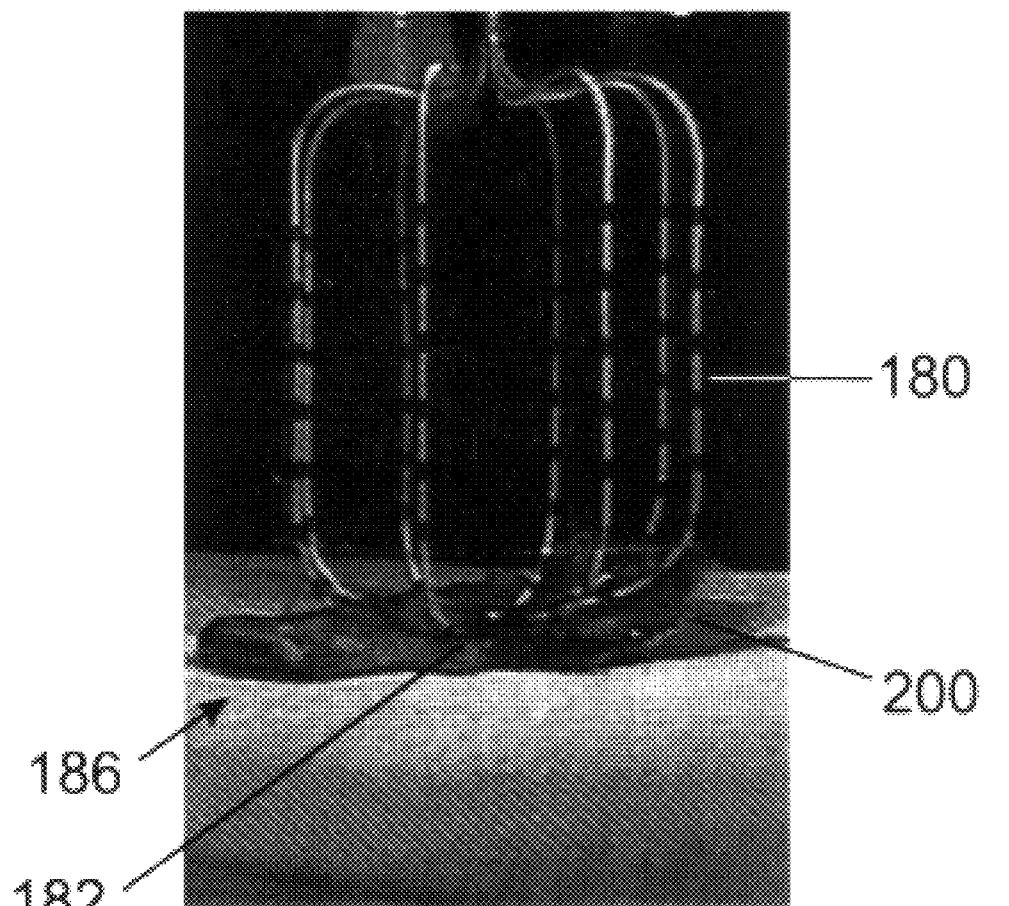

FIGS. 43A to 43E are successive photographs showing the preferred structure 186 during measurement of the tissue pressure function $T_p$, under comparable contact force conditions as FIGS. 42A to 42E for the other structure 190. FIG. 43A shows the distal tip 182 applying a contact force $F_c$ of 19 grams to a section of endocardial tissue 200 (lamb atrial tissue). FIGS. 43B and 43C show the distal tip 182 applying increasing contact forces $F_c$ of 50 grams and 79 grams, respectively. FIGS. 43D and 43E show the distal tip 182 applying a still increasing contact force $F_c$ of 140 grams and 168 grams, respectively.

FIGS. 43A to 43E show that continued application of the axial force upon the preferred structure 186 does not cause causes the splines 180 to buckle and warp. The lack of discontinuities in the radial stiffness function $S_r$ (FIG. 35) and axial stiffness function $T_f$ (FIGS. 37 to 39) indicated that this stability would be present.

FIGS. 43A to 43E also show that, as the contact force $F_c$ increases, the distal tip 182 of the preferred structure 186 incrementally increases the area of surface contact $A_{TIP}$. The increase in surface area $A_{TIP}$ distributes the increasing contact force $F_c$ to mediate tissue pressure $T_p$. As a result, the distal tip 182 of the preferred structure 186 does not protrude into the tissue 200. The position of the distal tip 182 against the surface of the tissue 200 remains essentially the same at both high and low contact forces.

FIGS. 43A to 43E also show that the absence of a complex curve configuration near the distal tip 182 of the preferred structure 186 holds the splines 130 surrounding the distal tip 182 in intimate contact with tissue.

Figure 41:
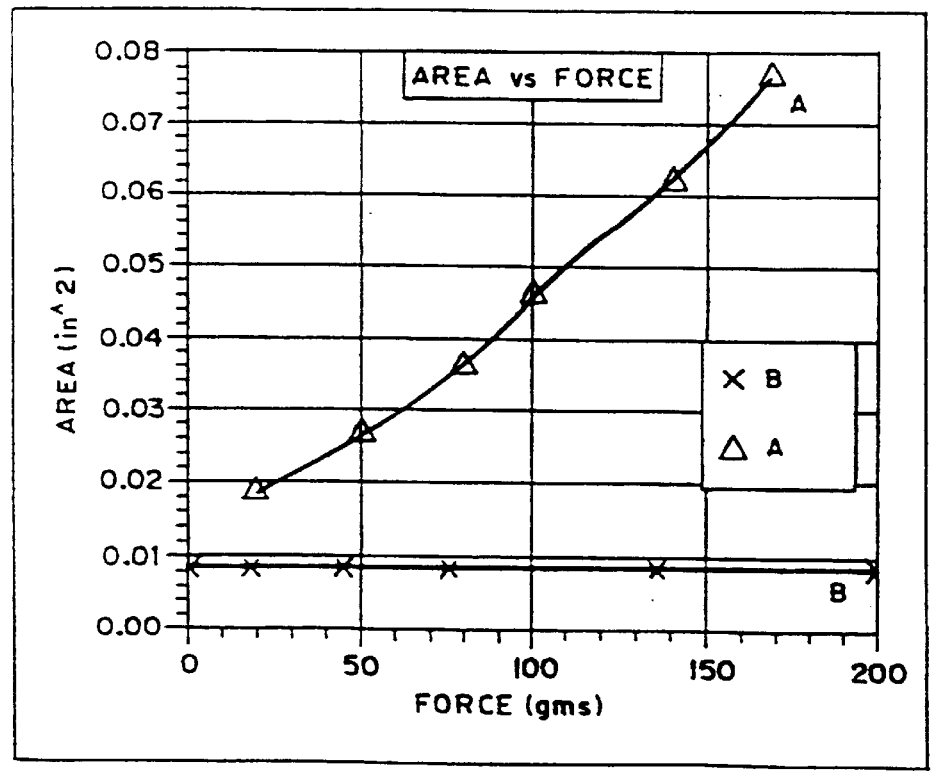
FIG. 41 is a graph comparing the distal tip area as a function of contact force for the preferred structure shown in FIG. 30 and the other structure shown in FIG. 34.

FIG. 41 plots the surface area of contact $A_{TIP}$ as a function of contact force $F_c$ for the preferred structure 186 (Curve A) and for the other structure 190 (Curve B). Curve A shows that, in the preferred structure 186, the surface area increases as the contact force rises. Curve B shows that, in the other structure 190, the surface area remains constant with increasing contact force. Curve B demonstrates that, in the other structure 190, surface area of contact is independent of axial force. Curve A demonstrates that, in the preferred structure 186, surface area and axial force change together to control tissue pressure.

The slopes of the tissue-pressure plots $\Delta T_p/\Delta F_c$ in FIG. 40 also determine the degree to which the surface area of contact $A_{TIP}$ changes to ameliorate tissue pressure with increasing contact force $F_c$. Plot B in FIG. 40 for the other structure 190 shows a steep, essentially constant slope for $\Delta T_p/\Delta F_c$, with $T_p$ increasing in a linear fashion with increasing $F_c$. This plot characterizes a stiff, javelin-like point of contact with tissue, which does not significantly change $A_{TIP}$ as $F_c$ changes. The photographs of FIGS. 42A to 42E confirm the validity of this indication. The photographs of FIGS. 42A to 42E also confirm the propensity of this type of distal tip structure 190 to protrude into tissue, thereby increasing the risk of tissue trauma and perforation.

On the other hand, Plot A in FIG. 40 shows a more shallow slope in the contact pressure that decreases in a nonlinear fashion with $T_p$. Plot A approaches a constant value despite increasing $F_c$. Plot A characterizes a more flexible region of tissue contact, in which the surface area of the contact increases with increasing $F_c$. The photographs of FIGS. 43A to 42E confirm the validity of this indication. The photographs of FIGS. 42A to 42E also confirm the propensity of this preferred type of distal tip structure 186 not to protrude into tissue, thereby diminishing the risk of tissue trauma and perforation.

Figure 29A:
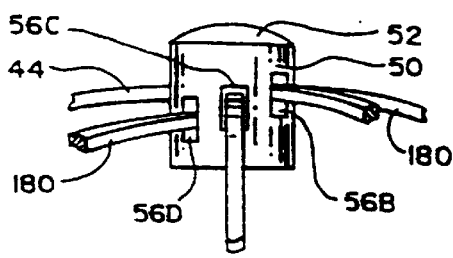
FIG. 29A is a side elevation view of the end cap shown in FIG. 25 with multiple hoop-like bodies shown in FIG. 23 secured in place to form an electrode support assembly.
Figure 29B:
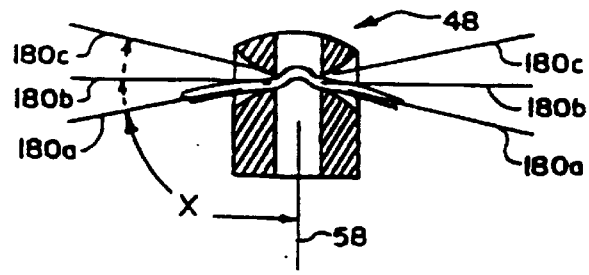
FIG. 29B is a diagrammatic view of the end cap shown in FIG. 25, demonstrating the preferred angular relationship between the spline elements and the end cap.

The preferred structure 186 of the preferred embodiment creates a larger distal surface area and thus reduces the overall magnitude of pressure exerted against tissue. As FIG. 29B show, the spline elements 180 of the preferred embodiment extend through the axis of the cap 48 at an angle χ that is greater than about 45° (as shown by phantom line spline elements 180a in FIG. 29B), but is less than about 110° (as shown by phantom line spline elements 180c in FIG. 29B). Preferably, the angle χ is between about 80° and 100°. In the illustrated preferred embodiment (as shown by spline elements 180b in FIG. 29B), the angle χ is about 90° (i.e., the spline elements 180c extend generally perpendicular to the axis of the cap 48).

As FIG. 30 shows, the angle χ that the cap 48 imposes creates an oval support structure 186 having a curvature that best approximates the contour of endocardial heart tissue. The oval structure 186 includes an enlarged, dome-shaped distal surface area 66 (see FIG. 30). The surface area 66 conforms intimately to endocardial tissue as the heart beats. The slotted cap 48 supports the distal ends of the spline elements 180 without imposing reverse or compound bends at the distal tip that force the spline elements 180 inward, out of the natural contour of heart tissue and into a geometrically unstable condition.

The slotted structure of the cap 48 makes possible the location of the distal-most spline elements 180 very close to the distal end of the cap 48. In the illustrated and preferred embodiment, the most distal slot 56A, through which the distal-most spline elements 180 extend, has a centerline that is separated from the distal end of the cap 48 by no more than about 0.040".

As a result (see FIG. 30), when the structure 136 is fully deployed for use, the cap 48 projects only a minimal distance beyond the envelope of the resulting structure 186. Practically speaking, the cap 48 lies essentially within the envelope of the distal surface area 66.

The geometry that the cap 48 permits creates a relatively smooth surface area 66 that is essentially free of major projections that can extend to a significant extent into endocardial tissue. The contour of the surface 66 extends along an essentially constant arc from one spline 180, across the end cap 48 to an opposite spline 180. The end cap 48 presents a surface 66 free of outward physiologically significant projections that can poke endocardial tissue to cause blunt tissue trauma. The contoured surface 66 extending about the cap 48 thus minimizes the chances of damage to endocardial tissue during use.

The contoured surface 66 permits access to and intimate contact with tissue in the apex of the heart, at the base of the ventricles. About 186% of infarcted heart tissue is found to lie within the apex. Therefore, providing non-traumatic access to this region offers considerable diagnostic benefit.

Furthermore, the alignment of the end cap 48 along this contoured surface 66 makes it possible to use the end-cap 48 itself as an electrode. The contour surface 66 and non-projecting end-cap 48 allow the physician to deploy the structure 186 and obtain electrogram signals from the apex of the heart using the end-cap as an electrode. Again, considerable diagnostic benefits result.

The features of the invention are set forth in the following claims.

We claim:

1. An electrode support structure comprising
   a hub, the hub having a side wall with an outer surface,
   a base aligned along a major axis with the hub,
   a generally flexible spline element extending between the hub and the base, the spline element extending from the base generally parallel to the major axis and, constrained by the hub to extend from the outer surface of the side wall at an angle, measured relative to the major axis, equal to or greater than 45°, and
   an electrode carried by the spline element.

2. A support structure according to claim 1
   wherein the hub includes a side wall located about the major axis, and
   wherein the spline element radiates outward from the side wall at the angle.

3. A support structure according to claim 1
   wherein the angle is between about 80° and about 100°.

4. A support structure according to claim 1
   wherein the angle is about 90°.

5. A support structure according to claim 1
   wherein the spline defines a distal surface which lies within an envelope at the hub, and
   wherein the hub lies generally within the envelope of the distal surface.

6. A support structure according to claim 1
   wherein the hub includes a slot that extends across the major axis, and
   wherein, at the hub, the spline element is constrained within the slot.

7. A support structure according to claim 1
   wherein the hub includes a slot that extends across the major axis, and
   wherein, at the hub, the spline element is constrained within the slot against movement out of the slot, the slot having clearance to accommodate twisting of the spline element about its axis within the slot in response to external force.

8. An electrode support structure comprising
   a hub having an axis and a side wall located about the axis, the hub including a slot that extends across the axis through the hub, and
   at least two diametrically opposed, generally flexible spline elements connected to the hub, the spline elements having a terminal ends spaced from the hub, the spline elements being integrally joined by an intermediate body that passes through the slot while the opposed spline elements radiate free of the slot, the intermediate body being flexibly constrained within the slot against movement out of the opening, the opening having clearance to accommodate twisting of the intermediate body within the slot in response to external force.

9. An electrode support structure comprising a hub, the hub having a side wall with an outer surface, a base aligned along a major axis with the hub and spaced at an established distance along the major axis from the hub, an array of generally flexible spline elements extending between the hub and the base, the spline elements each extending from the base generally parallel to the major axis and constrained by the hub to extend from the outer surface of the side wall at an angle, measured relative to the major axis, of between 45° and 110°, the spline elements flexing in response to an external force applied to the hub or the base along the major axis to shorten the established distance between the hub and the base, the spline elements collectively defining a distal surface lying within an envelope that approximates the curvature of endocardial tissue and within which envelope the hub lies, the distal surface, when contacting the endocardial tissue, increasing in surface areas in response to the force that shortens the established distance between the hub and the base to mediate tissue pressure.

10. A multiple electrode structure for deployment within the heart, comprising:

a hub having an axis and a side wall located about the axis, the side wall having an outer surfaces, and the hub having a distal end, an array of diametrically opposed, generally flexible spline elements connected to the outer surface of the side wall of the hub at an angle, measured relative to the axis of the hub, of between 45° and 110°, the spline elements having terminal ends spaced from the hub, electrodes carried by at least some of the spline elements, and a base joined to the terminal ends of the spline elements to flex the spline elements into a three dimensional, generally spheroid shape in which the hub and base are spaced an established distance apart along the axis, the generally spheroid shape having a distal surface lying within an envelope that approximates the curvature of endocardial tissue and within which envelope that distal end of the hub lies, the distal surface, when contacting endocardial tissue, increasing in surface area in response to force applied to the hub or the base generally along the axis of the hub which increases flexure of the spline elements and shortens the established distance between the hub and the base.

11. An electrode support structure comprising a distal hub, a proximal base aligned along a major axis with the distal hub, the distal hub including a slot that extends across the major axis, a generally flexible spline element constrained within the slot and extending between the distal hub and the proximal base, the spline element having an elongated axis that, at the proximal base, extends generally parallel to the major axis and, at the distal hub, extends at an angle, measured relative to the major axis, of between 45° and 110°, and an electrode carried by the spline element.

12. An electrode support structure comprising a distal hub, a proximal base aligned along a major axis with the distal hub, the distal hub including a slot that extends across the major axis, a generally flexible spline element constrained within the slot and by the proximal base into a shape that:

at the proximal base, extends generally parallel to the major axis, at the distal hub, extends generally at an angle, measured relative to the major axis, of between 45° and 110°, and between the proximal base and the distal hub, bows outward of the major axis, and an electrode carried by the spline element.

13. An electrode support structure comprising a distal hub, a proximal base aligned along a major axis with the distal hub, the distal hub including a slot that extends across the major axis, a generally flexible spline element constrained within the slot and extending between the distal hub and the proximal base, the spline element having an elongated axis that, at the proximal base, extends generally parallel to the major axis and, at the distal hub, extends at an angle, measured relative to the major axis, of between 45° and 110°, the spline element being constrained within the slot against movement out of the slot, the slot having clearance to accommodate twisting of the spline element about its axis within the slot in response to external force, and an electrode carried by the spline element.

14. An electrode support structure comprising a distal hub, a proximal base aligned along a major axis with the distal hub, the distal hub including a slot that extends across the major axis, a generally flexible spline element constrained within the slot and by the proximal base into a shape that:

at the proximal base, extends generally parallel to the major axis, at the distal hub, extends generally at an angle, measured relative to the major axis, of between 45° and 110°, and between the proximal base and the distal hub, bows outward of the major axis, the spline element being constrained within the slot against movement out of the slot, the slot having clearance to accommodate twisting of the spline element about its axis within the slot in response to external force, and an electrode carried by the spline element.

* * * * *